United States Patent
Ikehara et al.

(10) Patent No.: US 10,551,300 B2
(45) Date of Patent: Feb. 4, 2020

(54) OBSERVATION APPARATUS, OBSERVATION SYSTEM, DATA PROCESSING APPARATUS, AND PROGRAM

(71) Applicants: NATIONAL INSTITUTE OF ADVANCED INDUSTRIAL SCIENCE AND TECHNOLOGY, Chiyoda-ku, Tokyo (JP); NIKON CORPORATION, Minato-ku, Tokyo (JP)

(72) Inventors: Yuzuru Ikehara, Tsukuba (JP); Josaku Sakakima, Fujisawa (JP)

(73) Assignees: NATIONAL INSTITUTE OF ADVANCED INDUSTRIAL SCIENCE AND TECHNOLOGY, Tokyo (JP); NIKON CORPORATION, Tokyo (JP)

( * ) Notice: Subject to any disclaimer, the term of this patent is extended or adjusted under 35 U.S.C. 154(b) by 0 days.

(21) Appl. No.: 16/147,526

(22) Filed: Sep. 28, 2018

(65) Prior Publication Data
US 2019/0033203 A1 Jan. 31, 2019

Related U.S. Application Data

(63) Continuation of application No. PCT/JP2017/013156, filed on Mar. 30, 2017.

(30) Foreign Application Priority Data

Mar. 31, 2016 (JP) ................................ 2016-071650

(51) Int. Cl.
*G01N 21/21* (2006.01)
*G01N 21/3577* (2014.01)
(Continued)

(52) U.S. Cl.
CPC ........... *G01N 21/21* (2013.01); *A61B 5/0075* (2013.01); *A61B 5/14558* (2013.01);
(Continued)

(58) Field of Classification Search
CPC ... G01N 21/21; G01N 21/3577; A61B 5/0075
See application file for complete search history.

(56) References Cited

U.S. PATENT DOCUMENTS 7,999,231 B2   8/2011   Iguchi
9,829,380 B2   11/2017  Itoh
(Continued)

FOREIGN PATENT DOCUMENTS

JP    H04-3288449 A    11/1992
JP    H06-282791 A     10/1994
(Continued)

OTHER PUBLICATIONS

International Search Report and Written Opinion dated May 30, 2017 in corresponding International application No. PCT/JP2017/013156 with English translation.
(Continued)

*Primary Examiner* — Hugh Maupin
(74) *Attorney, Agent, or Firm* — Foley & Lardner LLP

(57) ABSTRACT

Provided is an observation apparatus that observes tissues of an organism. The observation apparatus includes a generator that generates first data obtained by irradiating the tissues with a first infrared light with a first wavelength and second data obtained by irradiating the tissues with a second infrared light with a second wavelength being different from the first infrared light in an optical property value with respect to a water, and a comparison calculator that compares the first data with the second data to generate bodily fluid data that indicates a presence of a bodily fluid on a surface of the tissues.

24 Claims, 26 Drawing Sheets

(51) Int. Cl.
  *A61B 5/00*     (2006.01)
  *A61B 5/1455*   (2006.01)
  *G01N 21/94*    (2006.01)

(52) U.S. Cl.
  CPC ....... *A61B 5/4283* (2013.01); *G01N 21/3577* (2013.01); *G01N 2021/945* (2013.01); *G01N 2201/0683* (2013.01)

(56) References Cited

U.S. PATENT DOCUMENTS

| | | |
|---|---|---|
| 2011/0306855 A1 | 12/2011 | Rabinovitz et al. |
| 2014/0200459 A1* | 7/2014 | Hendriks ................ A61B 1/00 600/477 |
| 2014/0285650 A1* | 9/2014 | Ishiwata ............ G06K 9/00127 348/79 |
| 2015/0099980 A1* | 4/2015 | Nahman .............. A61B 5/0075 600/475 |
| 2016/0249836 A1* | 9/2016 | Gulati .................. A61B 5/1455 600/316 |

FOREIGN PATENT DOCUMENTS

| | | |
|---|---|---|
| JP | 2006-102360 A | 4/2006 |
| JP | 2010-054457 A | 3/2010 |
| JP | 2012-005729 A | 1/2012 |
| JP | 2012-516186 A | 7/2012 |
| JP | 2014-25899 A | 2/2014 |
| WO | WO-2015/008435 A | 1/2015 |

OTHER PUBLICATIONS

Office Action received in corresponding Japanese Patent Application No. 2018-509411 dated Jul. 16, 2019 with English translation.

* cited by examiner (a)

÷  =

1070nm          1450nm (b)

÷  =

1260nm          1450nm (a) 1070nm/1450nm  (b) 1260nm/1450nm  (c) Visible Light Image After Bile Dropping (1070nm/1450nm) ÷ Before Bile Dropping (1070nm/1450nm) =

After Bile Dropping (1070nm/1450nm) − Before Bile Dropping (1070nm/1450nm) =

÷  =

After Bile Dropping (1070nm-1450nm)     Before Bile Dropping (1070nm-1450nm)

−  =

After Bile Dropping (1070nm-1450nm)     Before Bile Dropping (1070nm-1450nm)

Visible Light Image (a)

(b)

(a)

(b)

(c)

(a)                      (b)

After Blood Dropping (1260nm/1450nm) ÷ Before Blood Dropping (1260nm/1450nm) = R4

After Blood Dropping (1260nm/1450nm) − Before Blood Dropping (1260nm/1450nm) = R5

After Blood Dropping (1260nm-1450nm) ÷ Before Blood Dropping (1260nm-1450nm) = R6

After Blood Dropping (1260nm-1450nm) − Before Blood Dropping (1260nm-1450nm) = R7

(a)

Stage Scanning Direction

Without Polarizing Plate (b)

s Polarization, Parallel (c)

s Polarization, Crossed-Nicol (d)

p Polarization, Parallel (e)

p Polarization, Crossed-Nicol (a)

Without Polarizing Plate
(1070nm)

(b)

s Polarization, Parallel
(1070nm)

(c)

s Polarization,
Crossed-Nicol
(1070nm)

(d)

p Polarization, Parallel
(1070nm)

(e)

p Polarization,
Crossed-Nicol
(1070nm)

(f)

Visible Light Image (a)

Without Polarizing Plate (1070nm)

(b)

$s$ Polarization Crossed-Nicol (1070nm)

OBSERVATION APPARATUS, OBSERVATION SYSTEM, DATA PROCESSING APPARATUS, AND PROGRAM

CROSS REFERENCE TO RELATED APPLICATIONS

This is a Continuation of PCT International Application PCT/JP2017/013156 filed on Mar. 30, 2017, which in turns claims benefit of Japanese patent application 2016-071650 filed in Japan on Mar. 31, 2016. The entire contents of each of the above documents are hereby incorporated by reference into the present application.

TECHNICAL FIELD

The present invention relates to an observation apparatus, an observation system, a data processing apparatus, and a program.

BACKGROUND ART

There has been a request, for example, to determine a distribution and an outflow source (or an adhesion source) of a bodily fluid on a biological surface, for example, when the bodily fluid flows out or adheres to the biological surface, such as a tissue surface and an organ surface, during, for example, a surgery or medical practice, such as a treatment.

CITATION LIST

Patent Literature

Patent Literature 1: JP 2006-102360 A

SUMMARY OF INVENTION

However, for example, in a case of a bodily fluid that is difficult to be determined with a visible light (for example, with naked eyes), it has been difficult to determine, for example, the distribution and the outflow source of the bodily fluid.

With a first aspect of the present invention, there is provided an observation apparatus that observes tissues of an organism. The observation apparatus includes a generator and a comparison calculator. The generator generates first data and second data. The first data is obtained by irradiating the tissues with a first infrared light with a first wavelength. The second data is obtained by irradiating the tissues with a second infrared light with a second wavelength. The second infrared light is different from the first infrared light in an optical property value with respect to a water. The comparison calculator compares the first data with the second data to generate bodily fluid data that indicates a presence of a bodily fluid on a surface of the tissues.

With a second aspect of the present invention, there is provided an observation apparatus that observes tissues of an organism. The observation apparatus includes a data generator that compares first data with second data to generate bodily fluid data. The first data is based on a first optical property value obtained from the tissues. The second data is based on a second optical property value different from the first optical property value. The bodily fluid data indicates a presence of a bodily fluid whose main component is a water in the tissues.

With a third aspect of the present invention, there is provided a non-transitory computer-readable computer medium storing a program used for an observation apparatus that observes tissues of an organism. The program causes a computer to execute a step of generating first data and second data and a step of generating bodily fluid data by comparing the first data with the second data. The first data is obtained by irradiating the tissues with a first infrared light with a first wavelength. The second data is obtained by irradiating the tissues with a second infrared light with a second wavelength. The second infrared light is different from the first infrared light in an optical property value with respect to a water. The bodily fluid data indicates a presence of a bodily fluid on a surface of the tissues.

With a fourth aspect of the present invention, there is provided a data processing apparatus that processes data regarding tissues of an organism. The data processing apparatus includes a data generator and a comparison calculator. The data generator generates first data and second data. The first data is obtained by irradiating the tissues with a first infrared light with a first wavelength. The second data is obtained by irradiating the tissues with a second infrared light with a second wavelength. The second data is different from the first infrared light in an optical property value with respect to a water. The comparison calculator compares the first data with the second data to generate bodily fluid data that indicates a presence of a bodily fluid in the tissues.

With a fifth aspect of the present invention, there is provided an observation system. The observation system includes the observation apparatus of the first aspect or the second aspect described above and a display that displays the generated bodily fluid data.

The description encompasses a content disclosed in Japanese Patent Application No. 2016-071650 forming a basis for priority of this application.

BRIEF DESCRIPTION OF DRAWINGS

FIG. 16($b$) is a diagram illustrating exemplary wavelength dependences of logarithms of reciprocals of the reflectivities for viewing a difference between the bile and the blood.

FIG. 17($b$) and FIG. 17($c$) are diagrams illustrating exemplary images on which respective arithmetic processing, 1070 nm-1450 nm and 1070 nm/1450 nm, are performed.

FIG. 24($b$) is an exemplary s polarization crossed-Nicol image in FIG. 23($c$) with the wavelength of 1070 nm.

FIG. 25($b$) is an exemplary visible light image.

DESCRIPTION OF EMBODIMENTS

In this embodiment, a "bodily fluid" is a general term of a water contained within a body of an organism. The bodily fluid includes, for example, a bile, a pancreatic fluid, a blood, a lymph, a tissue fluid (an intertissue fluid, an intercellular fluid, and an interstitial fluid), and a celomic fluid. In this embodiment, the bodily fluid has a broad concept that includes a digestive juice.

"Bodily fluid data" includes data that "indicates the bodily fluid" and/or "highlights the bodily fluid."

An "optical property (value)" of an infrared light with respect to a water includes a rate of at least any energy of absorption, reflection, and transmission to an incident energy when a living body is irradiated with the infrared light. The optical property may be any optical property of absorption, reflection, and transmission as long as the optical property can be used when the living body is observed. While the following description uses the absorptance as an example for the optical property value, the optical property value is not limited to the absorptance, and a reflectivity and a transmittance may be used.

"Infrared data" includes data of the optical property obtained by irradiating tissues of an organism (for example, a living body) with the infrared light.

The "bodily fluid data" includes feature information of an organism (for example, a living body) specified (determined) by the observation apparatus, the observation system, or the like according to the embodiments.

The following describes the embodiments in details with reference to the diagrams.

First Embodiment

Figure 1A:
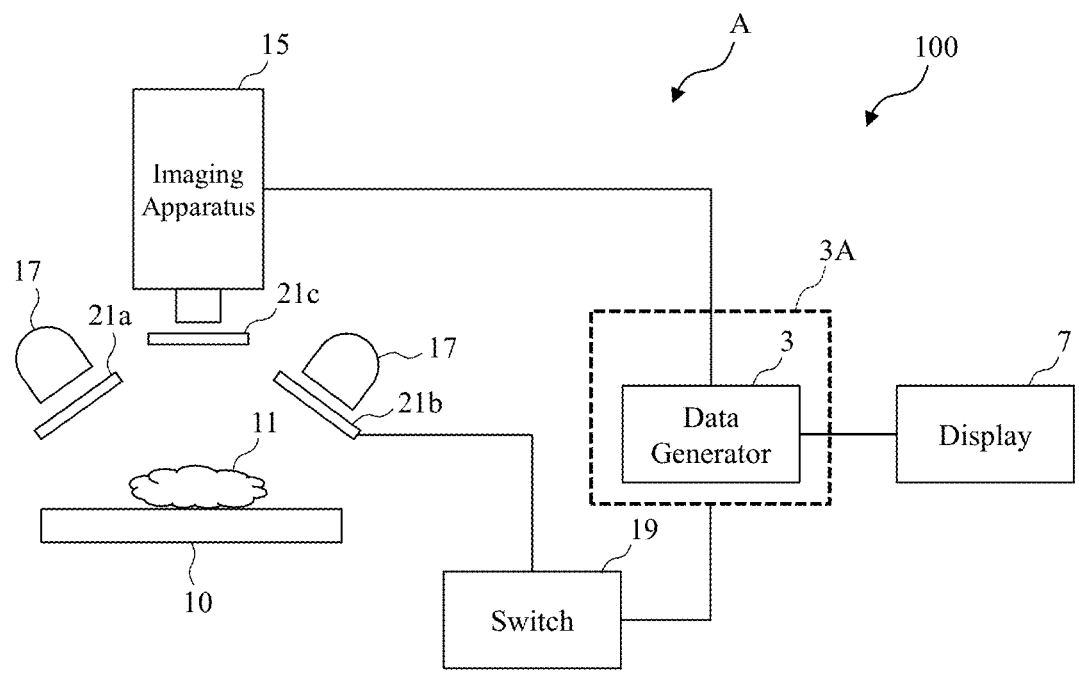
FIG. 1A is a function block diagram illustrating one exemplary configuration of an observation system illustrated as one example to which an observation technique according to a first embodiment is applied.

FIG. 1A is a function block diagram illustrating one exemplary configuration of an observation system (a biological evaluation system) 100 illustrated as one example of an observation technique according to a first embodiment. For example, the observation system (the biological evaluation system) 100 illustrated in FIG. 1A includes an observation apparatus (a biological evaluation apparatus) A and a display 7 coupled to the observation apparatus A such that a data communication can be made. For example, the observation apparatus (the biological evaluation apparatus) A includes a data generator 3, a stage 10, a light source apparatus 17, and an imaging apparatus (a detector, a sensor) 15. The data generator 3 generates data that highlights (or specifies) a bodily fluid or the like in a sample (an observation target) of biological tissues (biotissues or the like). A plate (or a dish) having tissues 11 made of the biological tissues (the biotissues) or a part of the biological tissues (the biotissues) is disposed on the stage 10. The light source apparatus 17 is for irradiating the tissues 11 made of the biological tissues (the biotissues) or a part of the biological tissues (the biotissues) placed on, for example, the plate or the stage 10 with an observation light, such as an infrared light (for example, a light with a predetermined wavelength selected from a wavelength band of 800 nm to 1600 nm, a wavelength band of 950 nm to 2000 nm or 800 nm to 2400 nm). The imaging apparatus 15 is, for example, a CCD camera that obtains an image of the tissues 11 as the observation target.

The detector 15 detects a detection result that is sent to the data generator 3.

A controller 3A includes, for example, the data generator 3. The observation apparatus A includes a polarizing plate 21, which will be described later. It should be noted that the observation apparatus A according to the embodiment may be configured without including the polarizing plate 21. The display 7 according to the embodiment may be a touch screen display or may be a portable terminal including a display. It should be noted that the stage 10 according to the embodiment may be configured to be relatively movable with respect to the light source apparatus 17 and the imaging apparatus 15.

It should be noted that a switch 19 will be described in a sixth embodiment.

Figure 1B:
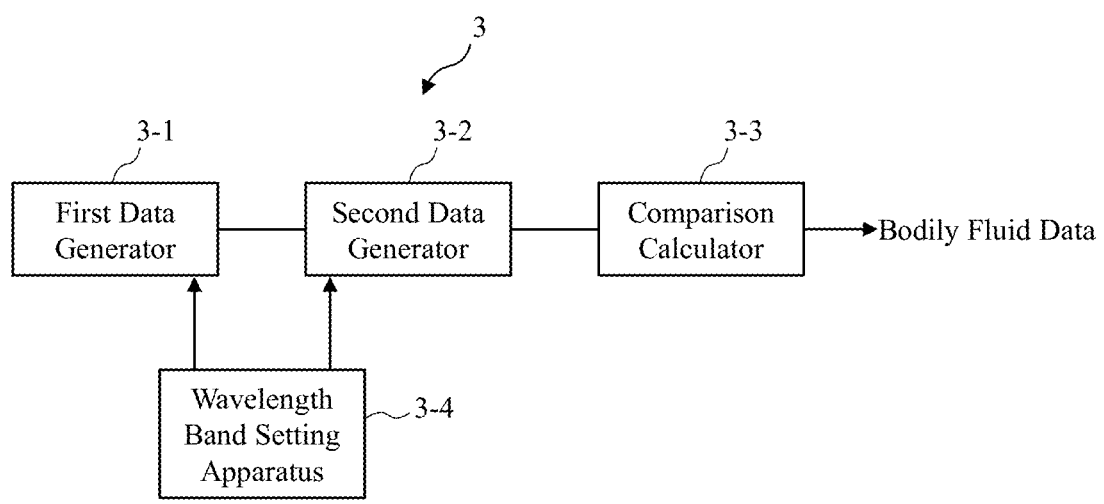
FIG. 1B is a function block diagram illustrating one exemplary configuration of a data generator according to the embodiment.

FIG. 1B is a function block diagram illustrating one exemplary configuration of the data generator (a biological information processing apparatus, a data processing apparatus) 3. The data generator 3 includes, for example, a first data generator 3-1, a second data generator 3-2, and a comparison calculator 3-3. The data generator 3 may be configured to include a wavelength band setting apparatus 3-4. The data generator 3 can be used as the biological information processing apparatus or the data processing apparatus. The biological information processing apparatus or the data processing apparatus functioning as the data generator 3 may have any of a software configuration and a hardware configuration, and can be configured of, for example, a computer and an integrated circuit that function independently from other components, such as the imaging apparatus 15 and the display 7.

The first data generator 3-1, for example, generates first data obtained by irradiating the tissues 11 of the organism with a first infrared light with a first wavelength whose optical property value with respect to a water (for example, an optical property value by a water, an absorptance of a light by a water, an absorptance of a light in a water, an optical property value of a water with respect to an infrared light with a predetermined wavelength) is a first optical property value (for example, a first absorptance). The second data generator 3-2 generates second data obtained by irradiating the tissues 11 of the organism with a second infrared light with a second wavelength whose optical property value with respect to a water (for example, an optical property value by a water, an absorptance of a light by a water, an absorptance of a light in a water, an optical property value of a water with respect to an infrared light with a predetermined wavelength) is a second optical property value (for example, a second absorptance) different from the first optical property value (for example, the first absorptance). The comparison calculator 3-3 performs an arithmetic operation that compares the first data and the second data sent from the first data generator 3-1 and the second data generator 3-2, respectively. The comparison calculator 3-3 generates bodily fluid data that indicates a presence of a bodily fluid on a surface of the tissues 11 from comparison data obtained as an arithmetic operation result. The bodily fluid data is converted, for example, in the comparison calculator 3-3, into data displayable on the display 7, and then sent to the display 7.

While it has been described an example where the comparison calculator 3-3 compares the data obtained by emitting the infrared lights with wavelengths having different optical property values of a water with respect to the infrared light here, the embodiment is not limited to such a configuration.

Thus, in the embodiment, it is possible to generate the bodily fluid data indicating the presence of the bodily fluid whose main component is, for example, a water in the tissues by the comparison calculator 3-3 comparing the first data based on the first optical property value obtained from the tissues with the second data based on the second optical property value different from the first optical property value in the observation apparatus that observes the tissues of the organism. The bodily fluid may include a bile or may include other bodily fluids. A generating technique of the bodily fluid data based on the optical properties according to the embodiment ensures clearly observing the bodily fluid, which is difficult to be determined with a visible light (for example, with naked eyes), thereby being usable as an important technique in a future medical treatment, such as a surgery and an inspection.

Arithmetic processing by the first data generator 3-1 will be described in details later. The wavelength band setting apparatus 3-4 sets wavelengths of the observation light (for example, the infrared light) with which the tissues 11 is irradiated in order to obtain the data generated in the first data generator 3-1 and the second data generator 3-2. The wavelengths set in the wavelength band setting apparatus 3-4 are sent to the first data generator 3-1 and the second data generator 3-2.

Figure 3:
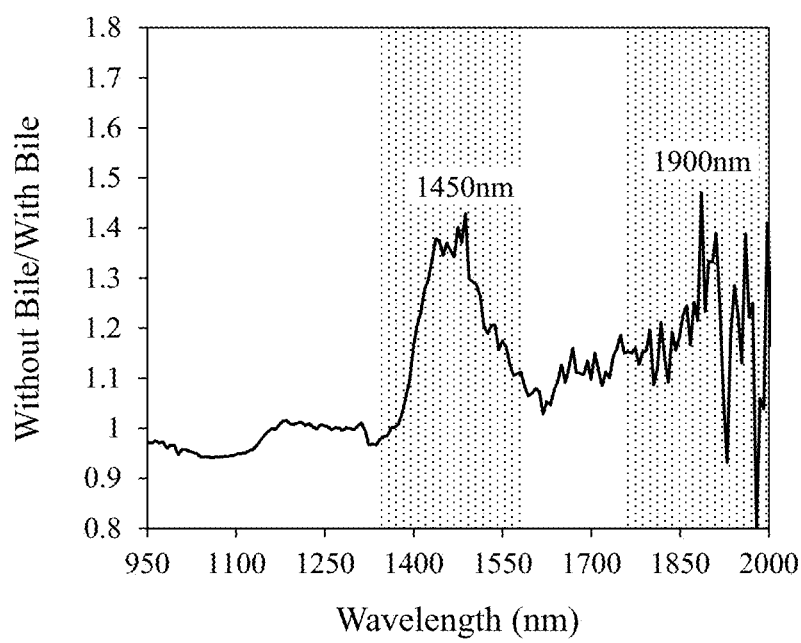
FIG. 3 is a diagram illustrating an exemplary absorption property (a wavelength dependence) that divides an absorptance of an infrared light in a case without a bile by an absorptance of an infrared light in a case with a bile according to the embodiment.
Figure 4:
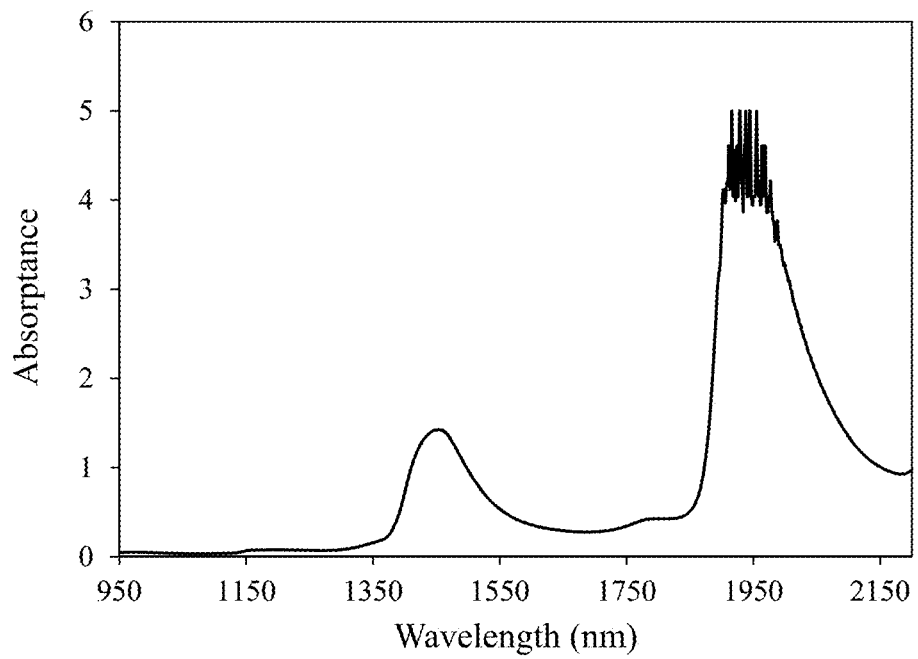
FIG. 4 is a diagram illustrating an absorption property (a wavelength dependence) of a water according to the embodiment.
Figure 5:
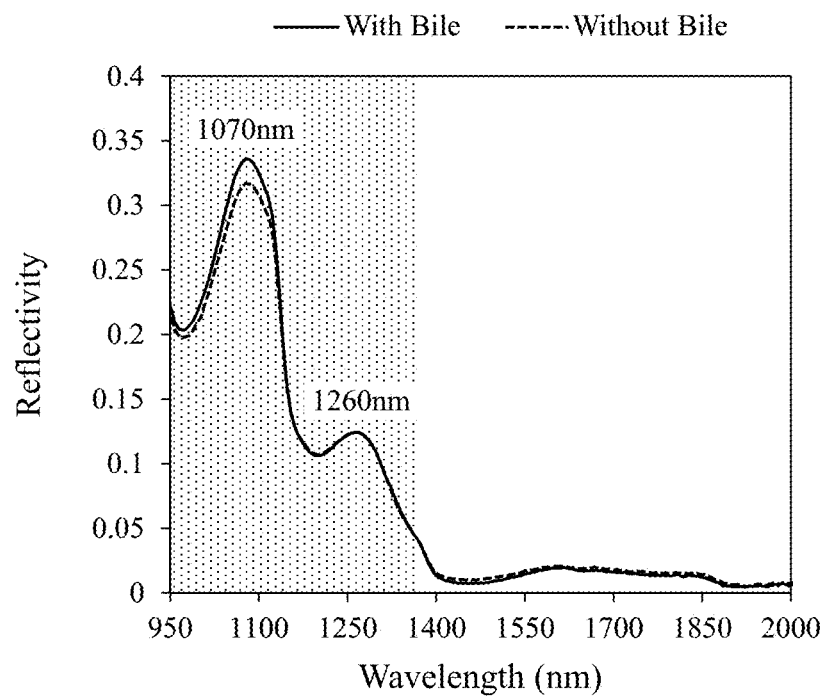
FIG. 5 is a diagram illustrating one example of wavelength dependences of reflectivities in the cases with the bile and without the bile according to the embodiment.

FIG. 5 is a diagram illustrating one example of wavelength dependences of reflectivities of the observation light (for example, the infrared light) in cases with a bile and without a bile on the surface of the tissues 11. As illustrated in FIG. 5, there is not much difference in spectra between with the bile and without the bile. However, by dividing an absorptance of the infrared light in the case without the bile by an absorptance of the infrared light in the case with the bile as illustrated in FIG. 3, there appears an absorption property (a wavelength dependence) similar to an infrared light absorption property (a wavelength dependence) of a water illustrated in FIG. 4. Accordingly, using the absorption property of the water with respect to the observation light (for example, the infrared light) is considered to be highly possible to determine presence/absence of the bile, which is difficult to be determined by a visual observation. For example, it is indicated that a distribution of the bodily fluid (the water) can be observed by comparing the two that are totally opposite, a wavelength (for example, near 1450 nm±50 nm or near 1900 nm±50 nm) having a large absorption by the water (small in reflection) and a wavelength, for example, near 1070 nm±50 nm or near 1260 nm±50 nm, having a small absorption by the water.

Figure 2A:
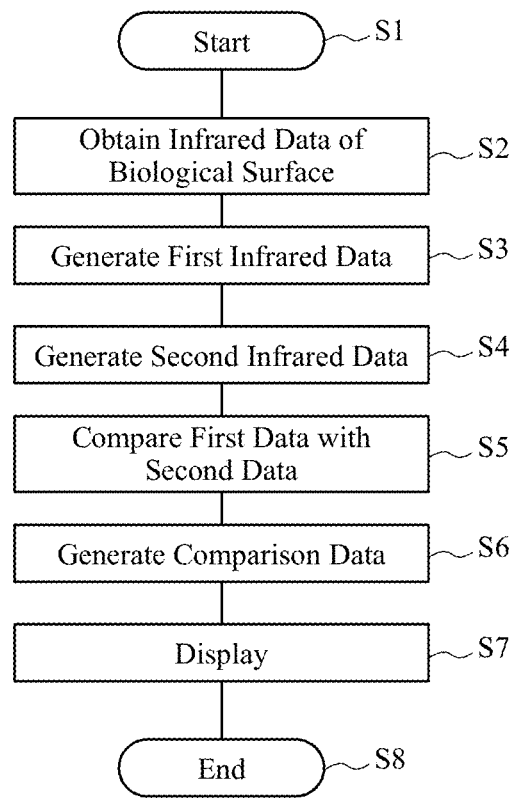
FIG. 2A is a flowchart diagram illustrating an exemplary procedure of a process by an observation system according to the embodiment.

FIG. 2A is a flowchart diagram illustrating an exemplary procedure of a process by the observation system 100. Here, a description will be given of an example where, for example, a liver and a gallbladder of a pig are observed as one example. A description will be given of an example to observe a distribution and an outflow source of a bile on a surface of an organism (for example, a biological surface and a tissue surface) where the bile as an example of the bodily fluids is flown out to the liver of the pig, using the observation system 100 of the embodiment.

First, the process starts at Step S1, and the observation apparatus A illustrated in FIG. 1A obtains infrared data of the surface of the organism (for example, the biological surface and a surface of the tissues 11) at Step S2.

It should be noted that the "absorptance of the infrared light or the like in the case without the bile" is, for example, an absorptance obtained by irradiating a portion without adherence or outflow of the bile on the surface of the tissues 11 with the observation light (for example, the infrared light). The "absorptance of the infrared light or the like in the case with the bile" includes, for example, an absorptance obtained by irradiating a portion with adherence or outflow of the bile on the surface of the tissues 11 with the observation light (for example, the infrared light).

Next, at Step S3, the first data generator 3-1 of the data generator 3 illustrated in FIG. 1B generates the first data (the first infrared data) obtained by irradiating the tissues 11 with the first infrared light based on the infrared data obtained from the observation apparatus A at Step S2. The first infrared light has an absorptance by the water (for example, an absorptance with respect to a water, an absorptance in a water, a rate of a light having a predetermined wavelength absorbed to a water, an absorptance of a water that differs by a wavelength of a light) that is the first absorptance. Next, at Step S4, the second data generator 3-2 of the data generator 3 illustrated in FIG. 1B generates the second data (the second infrared data) obtained by irradiating the tissues 11 with the second infrared light based on the infrared data obtained from the observation apparatus A at Step S2. The second infrared light has an absorptance by the water that is the second absorptance, which is different from the first absorptance. Here, the wavelength band setting apparatus 3-4 sets the wavelength bands, from which the infrared data are obtained from the observation apparatus A, in the first data generator 3-1 and the second data generator 3-2, such as the wavelength of 1070 nm±50 nm of the first infrared light and the wavelength of 1450 nm±50 nm of the second infrared light. Then, at Step S5, the comparison calculator 3-3 obtains the first data and the second data generated in the first data generator 3-1 and the second data generator 3-2 to perform their comparison operation, and at Step S6, generates bodily fluid data as comparison data obtained by the comparison operation between the first data and the second data. The bodily fluid data is sent to the display 7. At Step S7, the display 7 displays an image or the like based on the comparison data sent to the display 7. At Step S8, the process is terminated.

It should be noted that the comparison data may be identical to the bodily fluid data or the bodily fluid data may be data obtained as a result of appropriate image processing, such as a luminance adjustment, based on the comparison data.

Figure 6:
FIG. 6 includes diagrams exemplifying states, where comparison operations are performed on data having different setting wavelengths in a comparison calculator, as image data according to the embodiment.
Figure 6:
Figure 6:
Figure 6:
Figure 6:
Figure 6:
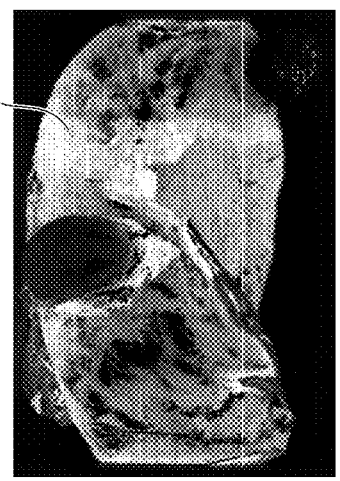

FIG. 6 includes diagrams exemplifying images that display results of comparison operations as image data on, for example, the display 7. The results of comparison operations are obtained such that the data (exemplarily illustrated in the image data) having mutually different setting wavelengths (or at least a part of the setting wavelengths) of the observation lights are compared in the comparison calculator 3-3 in the process described in FIG. 2A or the like above. FIG. 6(a) includes diagrams illustrating, in an order from a left side, a first observation image (a left diagram) obtained by irradiating tissues with an infrared light with the wavelength of 1070 nm, which is small in absorption by the water, a second observation image (a middle diagram) obtained by irradiating the tissues with the infrared light with the wavelength of 1450 nm, which is large in absorption by the water, and an image (hereinafter also referred to as a highlighted image) (a right diagram) based on bodily fluid data generated by dividing the first observation image by the second observation image.

FIG. 6(b) includes diagrams illustrating, in an order from the left side, a first observation image (a left diagram) obtained by irradiating tissues with an infrared light with a wavelength of 1260 nm, which is small in absorption by the water, a second observation image (a middle diagram) obtained by irradiating the tissues with the infrared light with the wavelength of 1450 nm, which is large in absorption by the water, and an image (a right diagram) based on bodily fluid (bile) data generated by dividing the first observation image by the second observation image.

It was found that the images based on the bodily fluid (bile) data can clearly distinguish regions R1 and R2, where the bile flew out, from other regions in both cases of the diagrams of FIGS. 6(a) and (b). The following similar diagrams also illustrate the images on which similar arithmetic processings have been performed.

Thus, the observation apparatus A ensures generating images based on the bodily fluid (bile) data by performing the above-described dividing processing in the comparison calculator 3-3.

Figure 7:
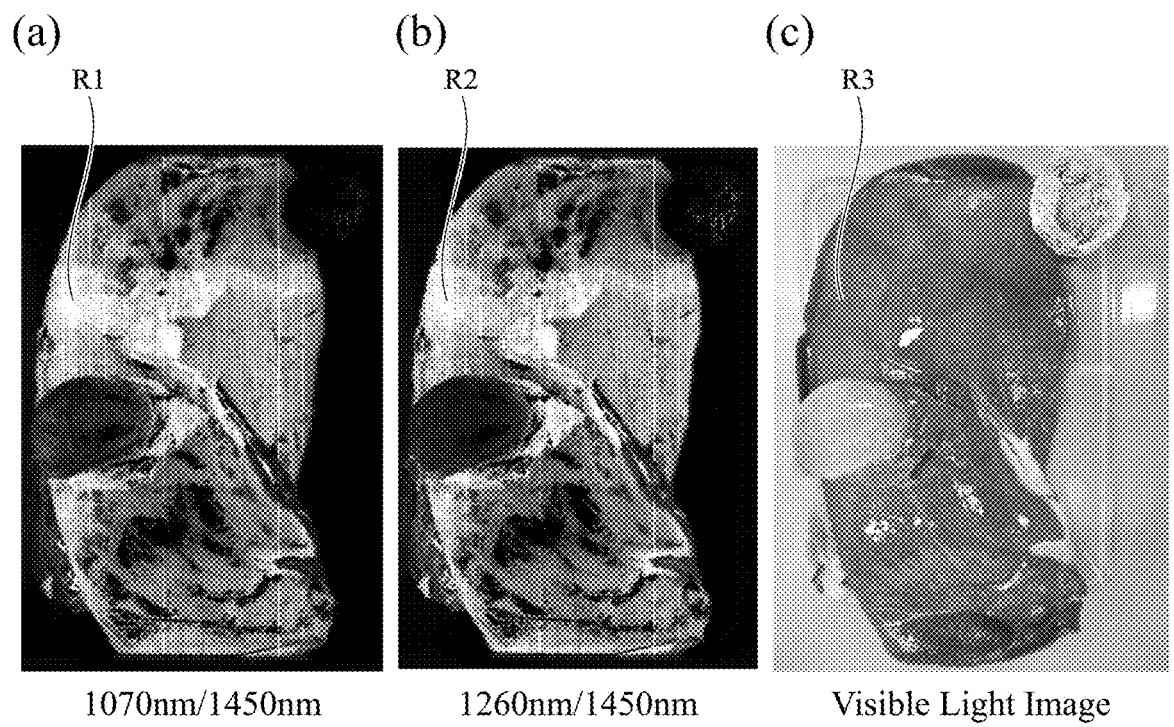
FIG. 7 includes diagrams in which two images based on bile data and a visible light image are compared according to the embodiment.

FIG. 7 includes diagrams in which two images based on these bodily fluid (bile) data and the image based on the visible light are displayed, for example, on the display 7 and are compared. As illustrated in FIG. 7, it is seen that the data generator 3 performing a process on a region R3 (FIG. 7(c)) where the bile, which is difficult to be distinguished in the image based on the visible light, is distributed can obtain images highlighted as the regions R1 (FIG. 7(a)) and R2 (FIG. 7(b)). It should be noted that, the reason that the region R3 where the bile is distributed is visually perceivable in the visible light image (FIG. 7(c)) is that a large amount of the bile is dropped in order to facilitate the comparison with the regions R1 and R2 in the highlighted images. During an actual surgery, it is difficult to visually perceive the distribution of the bile from the visible light image in many cases. While the arithmetic processing (for example, the comparison operation) according to the embodiment has been described as a division of the first data by the second data in the comparison calculator 3-3, as described later, the arithmetic processing according to the embodiment may be a subtraction (differential arithmetic processing) between the first data and the second data performed in the comparison calculator 3-3, or the arithmetic processing according to the embodiment is not limited to these operations as long as the operation ensures a comparison between the first data and the second data performed in the comparison calculator 3-3.

As described above, with the observation technique according to the embodiment, the observation apparatus A (the observation system 100) irradiates the surface of the tissues with the first and the second infrared lights having different optical properties of the water, and performs the data processing in the data generator 3. This ensures displaying and observing the bodily fluid (for example, the bile) or the like on the surface, on, for example, the display 7, even in a case where a determination of the bodily fluid is difficult with the observation technique based on the visible light, such as the distribution and the outflow source of the bodily fluid, such as the bile. Therefore, determining the distribution and the outflow source of the bodily fluid is facilitated.

It should be noted that the above-described embodiment has described an example where the bodily fluid is the bile. In the embodiment, a description has been made that the bodily fluid distribution can be observed by comparing the data of the wavelength having a large absorption by the water with the data of the wavelength having a small absorption by the water using the fact that near-infrared spectra of the bile and the water are approximate so as to ensure detecting the bodily fluid even when the difference of visible light spectral characteristics between the biological surface and the bodily fluid is small and when the flown-out bodily fluid has a minute amount. For example, when the main component of the bodily fluid is the water, the observation apparatus A according to the embodiment ensures detecting the bodily fluid distribution using a trend similar to that of the bile among the bodily fluids exemplified above.

Second Embodiment

Figure 8:
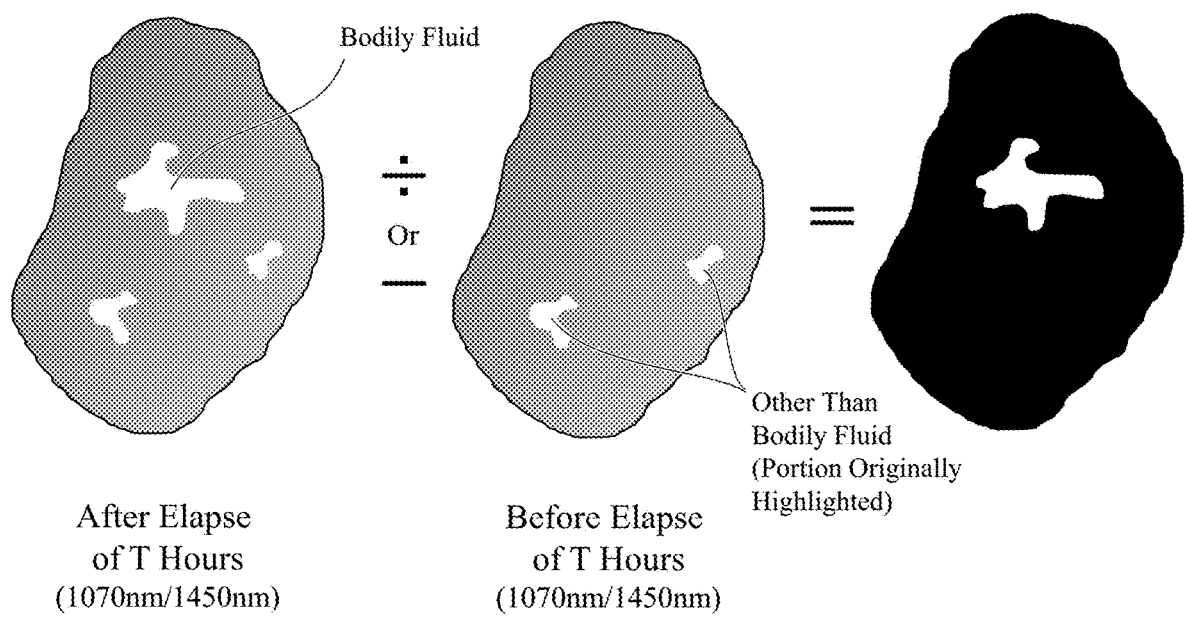
FIG. 8 is a diagram exemplarily illustrating a principle of an observation technique of tissues according to a second embodiment.

Next, a second embodiment will be described. FIG. 8 is a diagram exemplarily illustrating a principle of the observation technique of the tissues according to the embodiment.

As described in the first embodiment, only by the process of the comparison calculator 3-3 comparing the first data (for example, the first infrared data) with the second data (for example, the second infrared data) at a certain time point, there might be a case where it is difficult to determine whether the obtained bodily fluid data is based on an outflow of the bodily fluid of the tissues 11. It is because there is a case where it is unknown whether the highlighted region in the observation image is based on the bodily fluid of the tissues 11 or is a region originally highlighted by a factor other than the bodily fluid.

Figure 1C:
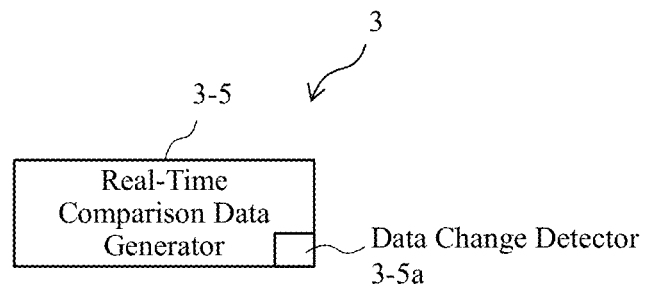
FIG. 1C is a diagram illustrating an exemplary configuration where a real-time comparison data generator is disposed in the data generator of an observation apparatus according to the embodiment.

Therefore, in the embodiment, for example, as illustrated in FIG. 1C, the data generator 3 of the observation apparatus according to the embodiment includes a real-time comparison data generator 3-5 in association with the comparison calculator 3-3. The real-time comparison data generator 3-5 ensures obtaining the bodily fluid data, outputs in FIG. 1B, before and after a time passes (for example, a first time point and a second time point), and then, comparing them.

Figure 2B:
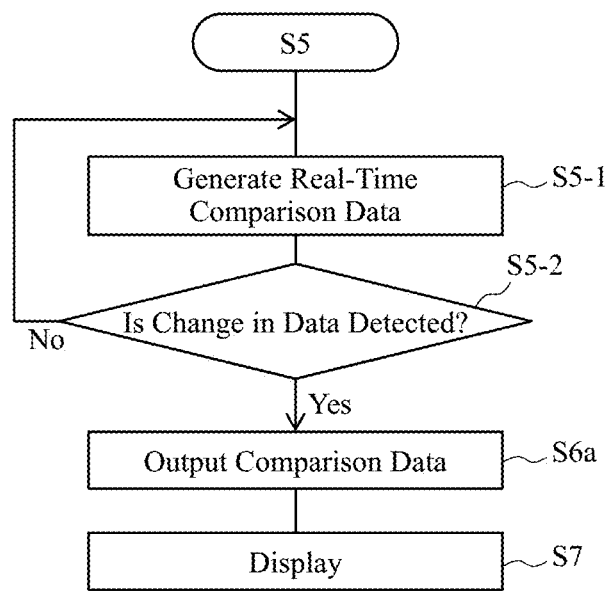
FIG. 2B is a flowchart diagram illustrating an exemplary procedure of the process at Step S5 in FIG. 2A.

FIG. 2B is a flowchart diagram illustrating an exemplary procedure of a process including the real-time comparison data generator 3-5.

When the comparison calculator 3-3 compares the first data with the second data generated in the first data generator 3-1 and the second data generator 3-2, respectively to obtain the comparison data at Step S5 in FIG. 2A, the real-time comparison data generator 3-5 generates the comparison data on a real-time basis (Step S5-1). Then, when a change in the data is detected at Step S5-2 (Yes), respective comparison data (time changing data) at different timings are obtained as illustrated at Step S6a, and these comparison data are further compared by an operation to obtain comparison data. Then, image data based on this comparison data is sent to the display 7, and the display 7 displays an image or the like at Step S7.

Two pieces of data as the left diagram and the middle diagram in FIG. 8 are the real-time comparison data at Step S5-1. In the arithmetic processing at Step S6a, the data (the left diagram), which is obtained by dividing the data observed with the infrared light having 1070 nm at a different timing, for example, after an elapse of T hours by the data observed with the infrared light having 1450 nm, is divided or subtracted by the data (the middle diagram), which is obtained by dividing the data observed with the infrared light having 1070 nm, for example, before the elapse of T hours by the data observed with the infrared light having 1450 nm (Step S6a). This ensures obtaining only data based truly on the bodily fluid as in the right diagram in FIG. 8.

In the above-described process, the first data generator 3-1 and the second data generator 3-2 obtaining the respective data before the elapse of T hours and after the elapse of T hours at a predetermined time interval or any time interval, and then, for example, comparing the two (the respective data) in the real-time comparison data generator 3-5 ensure the image data that highlights the bodily fluid. A time after the elapse of T hours may be a timing at which, for example, an observer visually observes the bodily fluid flowing out.

FIG. 9A to FIG. 10B are diagrams illustrating various examples of arithmetic processing for highlight processing of bodily fluid data by operations of data obtained at different timings in the real-time comparison data generator 3-5.

The following describes each of the arithmetic processing.

Figure 9A:
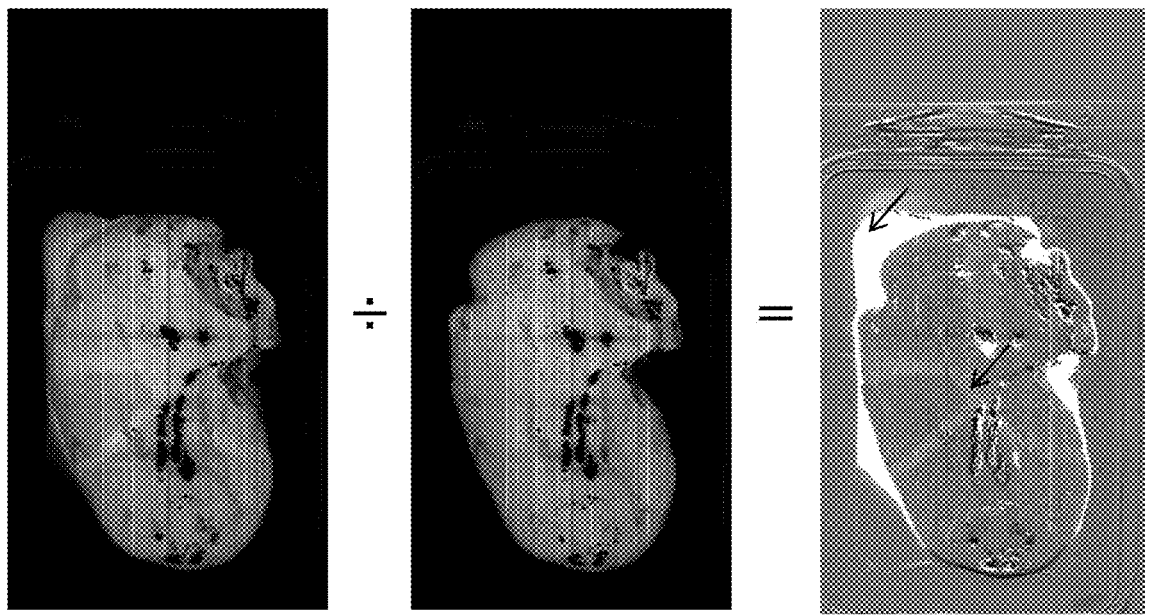
FIG. 9A is a diagram illustrating exemplary images obtained by arithmetic processing for highlight processing of bodily fluid data according to the embodiment.
Figure 9B:
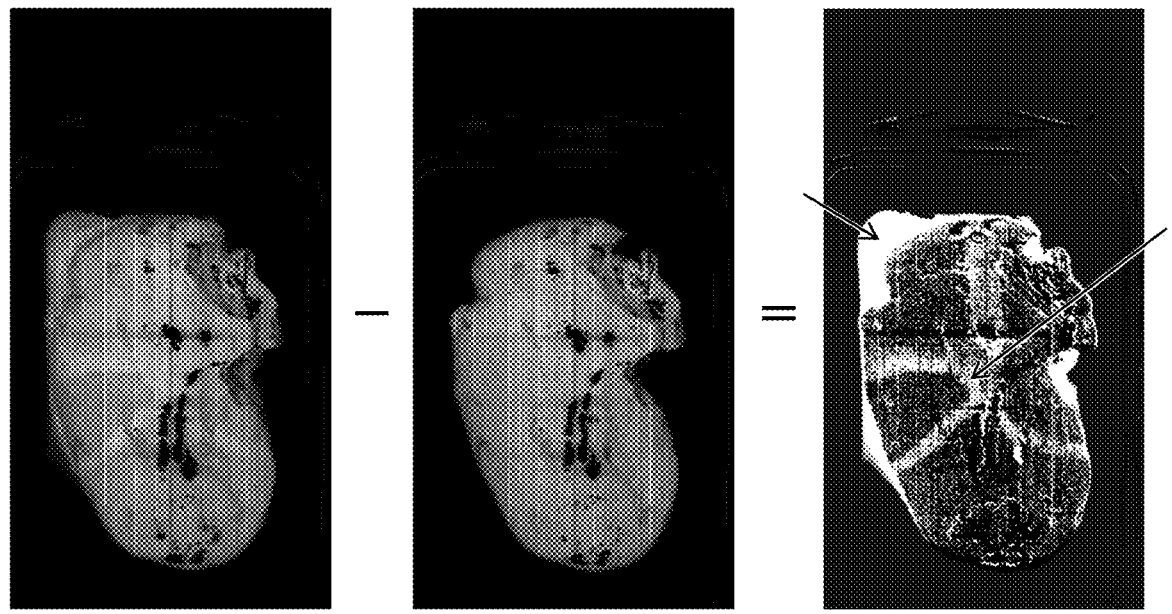
FIG. 9B is a diagram illustrating exemplary images obtained by arithmetic processing for highlight processing of bodily fluid data according to the embodiment.

1) FIG. 9A: (an arrow indicates a bile region, and the same applies below).

Data after bile dropping: data obtained by dividing the first data with the infrared light having the wavelength of 1070 nm by the second data with the wavelength of 1450 nm.

Data before bile dropping: data obtained by dividing the first data with the infrared light having the wavelength of 1070 nm by the second data with the wavelength of 1450 nm.

Data on the right side obtained by dividing the data after the bile dropping by the data before the bile dropping reflects a distribution of the bile.

2) FIG. 9B:

Data after bile dropping: data obtained by dividing the first data with the infrared light having the wavelength of 1070 nm by the second data with the wavelength of 1450 nm.

Data before bile dropping: data obtained by dividing the first data with the infrared light having the wavelength of 1070 nm by the second data with the wavelength of 1450 nm.

Data on the right side obtained by subtracting the data before bile dropping from the data after bile dropping reflects a distribution of the bile.

3) FIG. 10A:

Data after bile dropping: data obtained by subtracting the second data with the wavelength of 1450 nm from the first data with the infrared light having the wavelength of 1070 nm.

Data before bile dropping: data obtained by subtracting the second data with the wavelength of 1450 nm from the first data with the infrared light having the wavelength of 1070 nm.

Data on the right side obtained by dividing the data after bile dropping by the data before bile dropping reflects a distribution of the bile.

4) FIG. 10B:

Data after bile dropping: data obtained by subtracting the second data with the wavelength of 1450 nm from the first data with the infrared light having the wavelength of 1070 nm.

Data before bile dropping: data obtained by subtracting the second data with the wavelength of 1450 nm from the first data with the infrared light having the wavelength of 1070 nm.

Data on the right side obtained by subtracting the data before bile dropping from the data after bile dropping reflects a distribution of the bile.

Figure 10A:
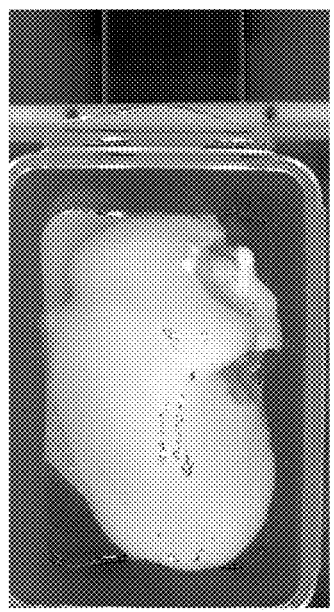
FIG. 10A is a diagram illustrating exemplary images obtained by arithmetic processing for highlight processing of bodily fluid data according to the embodiment.
Figure 10A:
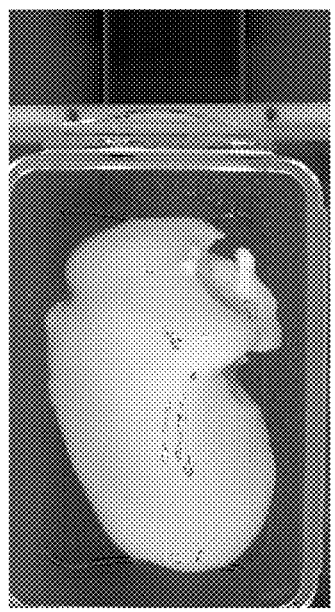
Figure 10A:
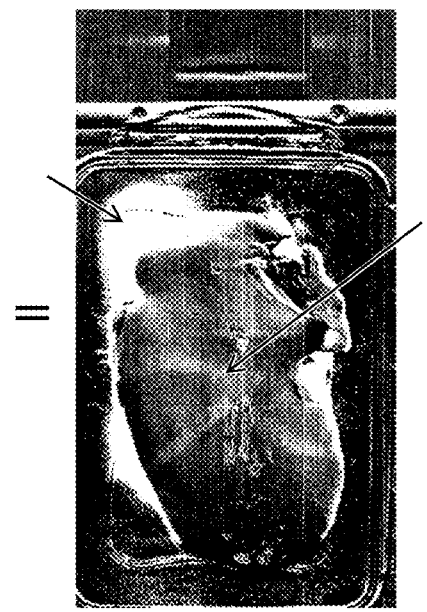
Figure 10B:
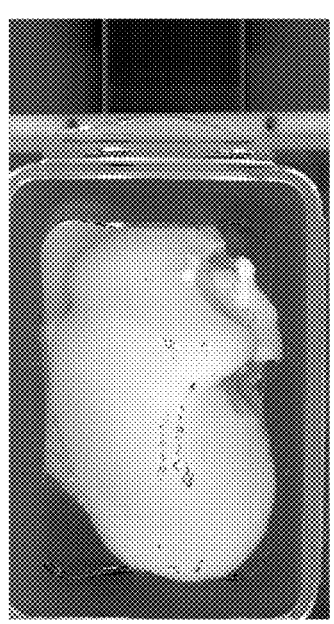
FIG. 10B is a diagram illustrating exemplary images obtained by arithmetic processing for highlight processing of bodily fluid data according to the embodiment.
Figure 10B:
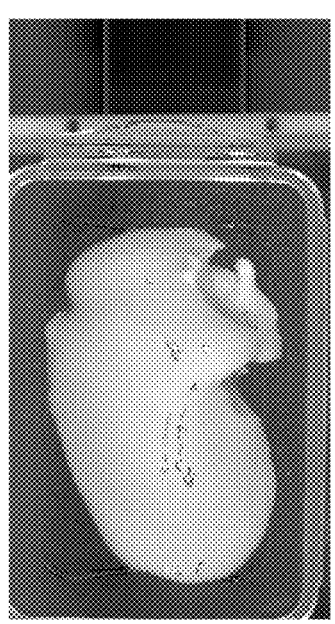
Figure 10B:
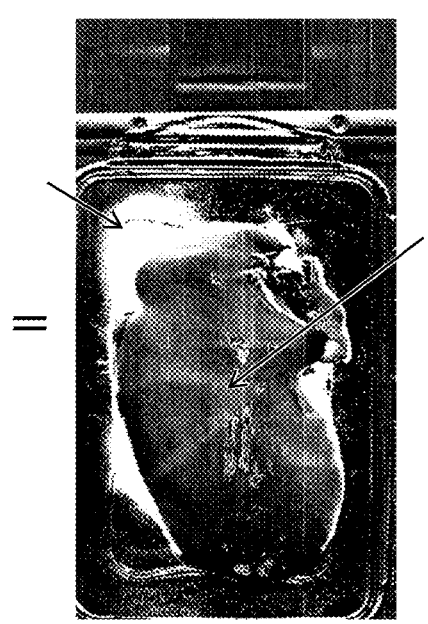
Figure 10C:
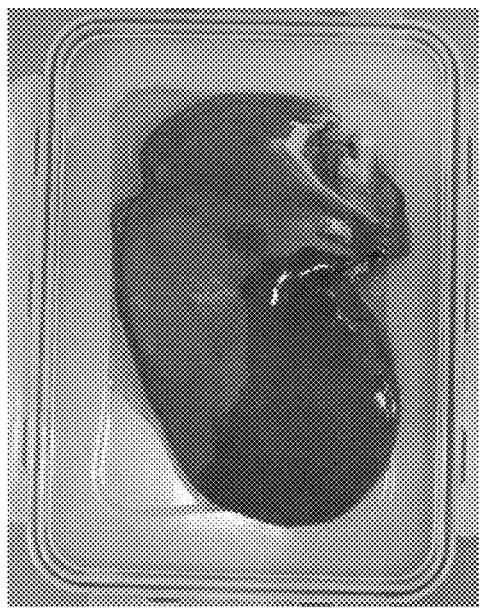
FIG. 10C is a diagram illustrating an exemplary visible light image according to the embodiment.

5) FIG. 10C: a visible light image. In the visible light image, it is difficult to visually perceive a distribution range of the bile dropped on a surface of a liver.

As described above, the observation apparatus A (or the observation system 100) of the embodiment obtains the data (for example, the image data) before the elapse of T hours (the first timing) and after the elapse of T hours (the second timing) at the predetermined time interval or any time interval and compares the two, thus ensuring highlighting the bodily fluid. A time after the elapse of T hours may be the timing at which, for example, the observer visually observes the bodily fluid flowing out to the surface of the tissues 11. Based, for example, on a plurality of pieces of data (for example, two pieces of data, three pieces of data, four pieces of data, five pieces of data, or ten pieces of data) obtained at the different timings, such as the data (for example, the image data) before the elapse of T hours (the first timing) and the data (for example, the image data) after the elapse of T hours (the second timing), the observation apparatus A (or the observation system 100) of the embodiment calculates chronological data of the plurality of pieces of data (for example, a plurality of pieces of the image data). Thus, an effect of a portion other than the bodily fluid (for example, a noise) can be reduced and the bodily fluid in the bodily fluid data can be highlighted.

Third Embodiment

In this embodiment, in addition to the above-described process (the second embodiment), an observation apparatus B generates data for live display based on the image data obtained by performing arithmetic processing on a plurality of pieces of the bodily fluid data. For example, during a surgery on a patient, the observation apparatus B can obtain the bodily fluid data before the elapse of T hours and after the elapse of T hours at the predetermined time interval or any time interval, and highlight the bodily fluid (for example, a bile and a blood) based on the two.

This embodiment performs the live display (moving image processing) that causes the display 7 to continuously display a motion of the bodily fluid, for example, on a real-time basis based on the bodily fluid data obtained in the second embodiment.

Figure 11A:
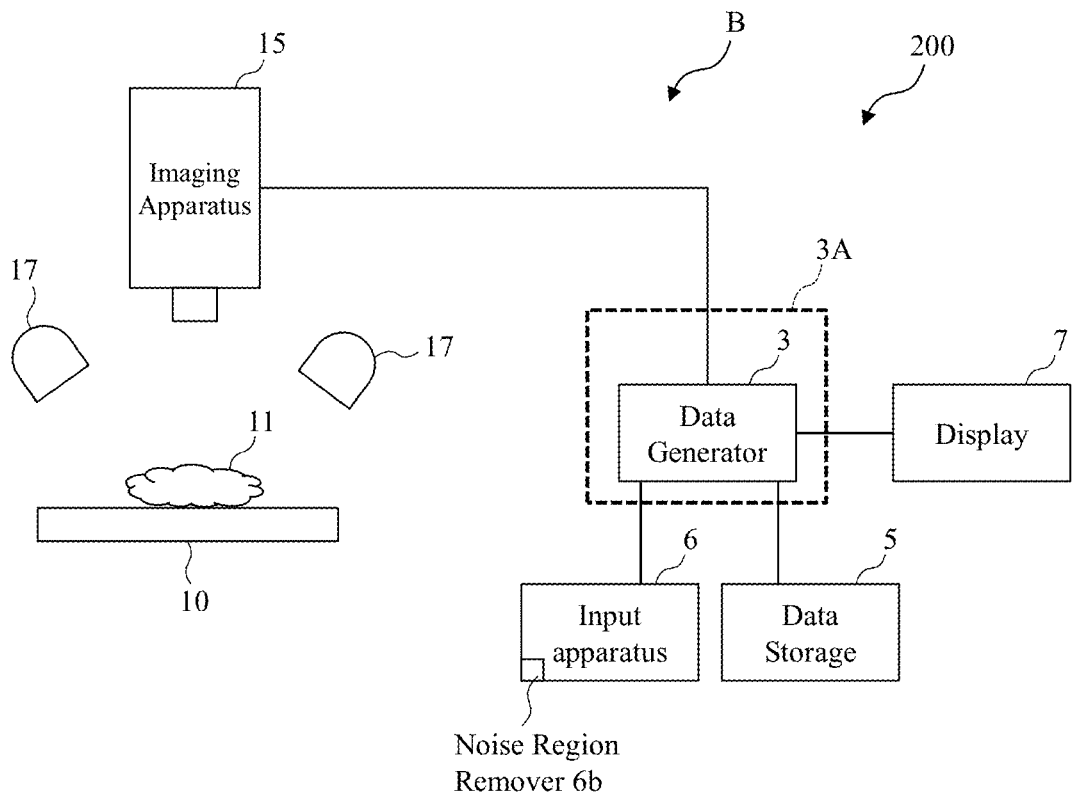
FIG. 11A is a function block diagram illustrating one exemplary configuration of the observation system according to the embodiment.

FIG. 11A is a function block diagram illustrating one exemplary configuration of the observation system according to the embodiment and is a modified diagram of FIG. 1A.

For example, an observation system (a biological evaluation system) 200 illustrated in FIG. 11A includes the observation apparatus (the biological evaluation apparatus) B and the display 7 coupled to the observation apparatus B such that a data communication can be made.

Figure 11B:
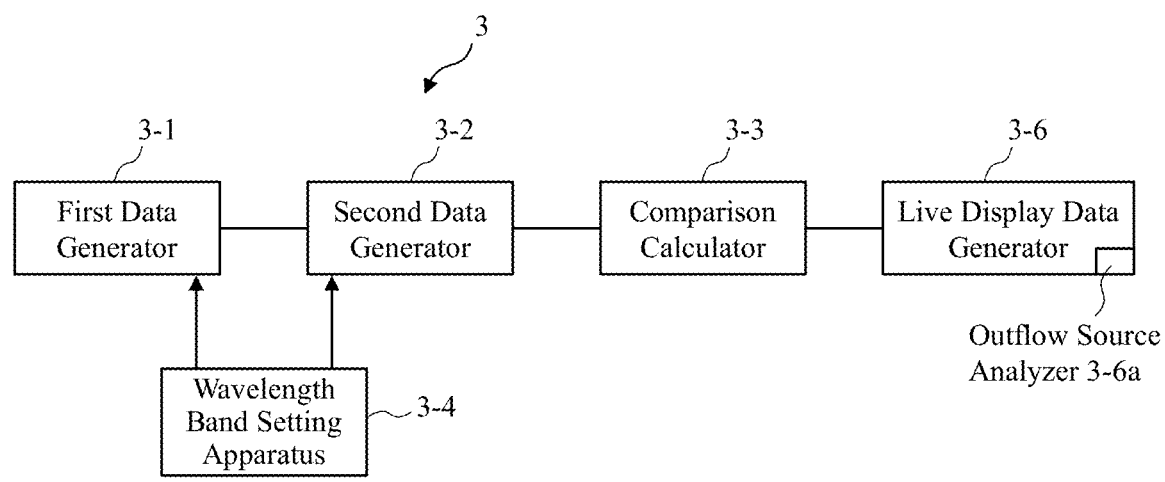
FIG. 11B is a function block diagram illustrating one exemplary configuration of the data generator of the observation system according to the embodiment.

FIG. 11B is a function block diagram illustrating one exemplary configuration of the data generator (the biological information processing apparatus, the data processing apparatus) 3. As illustrated in FIG. 11B, the data generator 3 for the comparison data (the bodily fluid data) according to the embodiment includes a live display data generator 3-6 that generates the data for live display based on the generated bodily fluid data. The live display data generator 3-6 includes an outflow source analyzer (an analyzer) 3-6a. For example, the outflow source analyzer 3-6a estimates and specifies a source of leakage (a source of leaking fluid) of a leaking fluid (such as the bodily fluid, the bile) on the surface of the tissues 11 using the data for the live display.

The bodily fluid data according to the embodiment is, for example, data (data of a highlighted image) obtained by a subtraction (the first wavelength–the second wavelength) or a division (the first wavelength/the second wavelength) between the respective images in the wavelength of 1070 nm (the first wavelength) and the wavelength of 1450 nm (the second wavelength) generated in the above-described embodiment. While the following describes an example of the bodily fluid data obtained by the division, the subtraction can obtain a similar result. It should be noted that, the bodily fluid data includes data (data of a highlighted image) obtained by performing arithmetic processing on each image obtained using a light with a wavelength selected from the above-described wavelength band of the infrared light.

Furthermore, the observation apparatus (the biological evaluation apparatus) B includes a data storage 5 that stores, for example, the bodily fluid data generated in the data generator 3. The data storage 5 may be a temporal memory, for example, a buffer memory.

Furthermore, the observation apparatus (the biological evaluation apparatus) B includes an input apparatus (including, for example, a GUI) 6.

The live display data generator 3-6 generates the data for live display based on the first bodily fluid data at the first timing and the second bodily fluid data at the second timing, which is different from the first timing.

The following describes a content of a generation process of live display data in the live display data generator 3-6 in relation to first and second generation process examples.

First Generation Process Example

First, a description will be given of a first generation process example according to the embodiment. In the first generation process example, the live display data generator 3-6 generates data for live display based on difference data between, for example, a first image (the bodily fluid data) taken at the first timing (for example, one or a plurality of timings $T_0$ to $T_6$ in FIG. 12) and a second image (the bodily fluid data) taken at a timing different from the first timing (for example, one or the plurality of timings $T_0$ to $T_6$ in FIG. 12). It should be noted that in the data generation process for live display, division data may be used instead of the above-described difference data.

Figure 12:
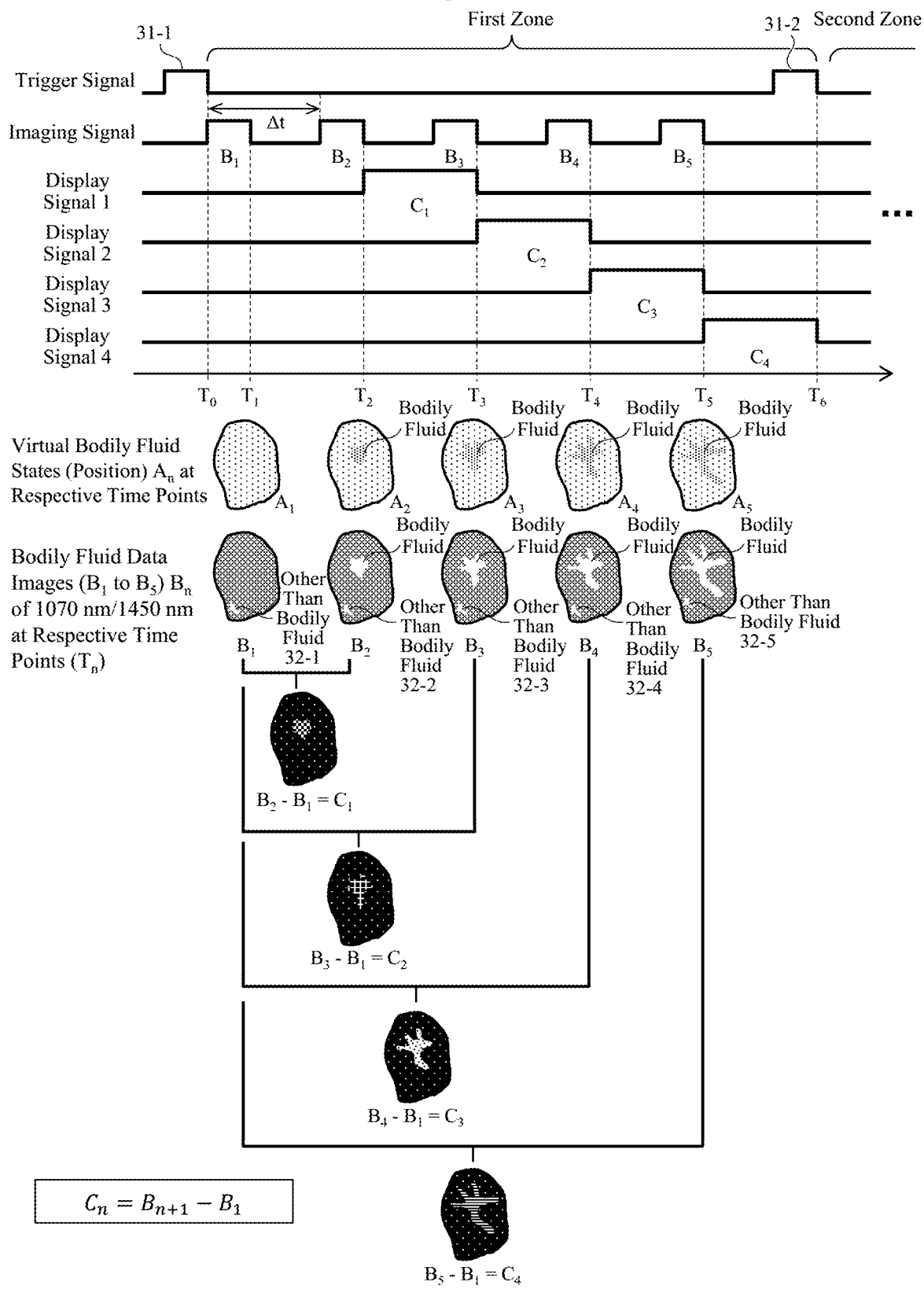
FIG. 12 includes a timing chart diagram (an upper diagram) illustrating output timings of images by imaging signals in a first generation process example and moving image data for live display, and a diagram (a lower diagram) illustrating images generated at the respective timings, according to the embodiment.

FIG. 12 includes a timing chart diagram (an upper diagram) illustrating output timings of images by imaging signals in the first generation process example and moving image data for live display and a diagram (a lower diagram) illustrating the bodily fluid data (images) generated at the respective timings. This timing chart diagram assumes a condition where the bodily fluid leaks at a time point of $T_2$ and the leaked bodily fluid expands on the tissues as the time passes.

Figure 13:
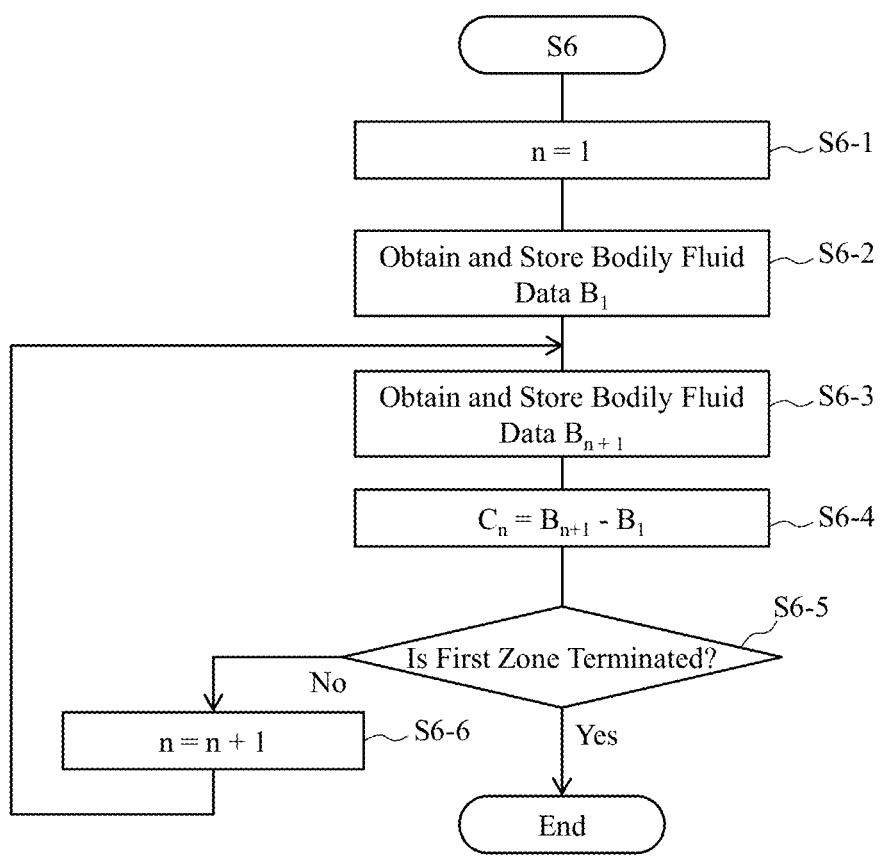
FIG. 13 is a flowchart diagram illustrating an exemplary procedure of a process in the first generation process example according to the embodiment.

FIG. 13 is a flowchart diagram illustrating an exemplary procedure of a process in the first generation process example. FIG. 13 illustrates a procedure of a process after generating the bodily fluid data at Step S6 in FIG. 2A.

When trigger signals 31-1, 31-2, or the like (for example, a signal of a process start and a signal of a process termination) illustrated in FIG. 12 are output, the bodily fluid data (1070 nm/1450 nm) at a timing $T_1$ is obtained as, for example, an image $C_1$ based on the imaging signal. At the timing $T_1$, while the bodily fluid is not leaked on the tissues as illustrated with a reference numeral $B_1$, there is a case where a portion other than the bodily fluid is highlighted due to the absorption property even in a portion other than the bodily fluid, and this appears in the image of the bodily fluid data as a noise region on the image. It should be noted that in images $B_n$ other than the image $B_1$, data based on the bodily fluid and data other than the bodily fluid (a noise region 32-n) are illustrated.

It should be noted that FIG. 12 has an upper row (below the timing chart) where images $A_n$ of virtual bodily fluid states are illustrated in schematic diagrams.

"Bodily fluid data" $B_1$, $B_2$, $B_3$, $B_4$, and $B_5$ based on the imaging signals illustrated in FIG. 12 are basic data for images $C_1$, $C_2$, $C_3$, and $C_4$. Performing similar arithmetic processing (for example, an addition) for several times on $C_1$, $C_2$, $C_3$, and $C_4$ generated by the arithmetic processing (for example, the subtraction, the division) as the respective images having one frame can obtain a plurality of frames (a stack). Connecting the plurality of frames makes the moving image data (the data for live display) in a predetermined zone (for example, a first zone, a second zone). Then, the data generator 3 causes the display 7 to display the moving image based on these image data.

Next, a description will be given of FIG. 13. First, when the trigger signal is output by an operation of the input apparatus 6, the live display data generator 3-6 performs an initialization with n=1 at Step S6-1.

Next, at Step S6-2, the live display data generator 3-6 obtains the bodily fluid data $B_1$ at, for example, the timing $T_1$ and stores the bodily fluid data $B_1$ in the data storage 5. In the embodiment, this is referred to as reference data $B_1$. It should be noted that the reference data may be a reference image.

At Step S6-3, the live display data generator 3-6 obtains the bodily fluid data $B_2$ after $\Delta t$, that is, at the timing $T_2$, and temporarily stores the bodily fluid data $B_2$ and the obtained timing in, for example, the data storage 5. At this time, the live display data generator 3-6 causes the data storage 5 to store the bodily fluid data $B_2$ in a region different from a region where the reference image $B_1$ is stored at Step S6-2.

At Step S6-4, the live display data generator 3-6 generates difference data $C_n=B_{n+1}-B_1$ that is difference data $C_1=B_2-B_1$ here. This difference data $C_1$ is displayed as a first frame of the live display on the display 7. The live display data generator 3-6 causes the data storage 5 to store the difference data $C_1$ in a region for the live display.

These difference data $C_n$ are illustrated on the lower four rows in the bodily fluid data in FIG. 12 (n=1 to 4).

The live display data generator 3-6 taking the difference data between the bodily fluid data $B_1$ stored in the data storage 5 and the bodily fluid data $B_{n+1}$ at the respective timings as indicated in Formula (1) ensures obtaining the difference data $C_n$ from which portions other than the bodily fluid are removed.

[Formula 1]

$$C_n = B_{n+1} - B_1 \tag{1}$$

At Step S6-5, the live display data generator 3-6 determines whether the first zone in FIG. 12 has been terminated, that is, whether the trigger signal 31-2 that instructs a termination of the live display of the leakage fluid has been output. When the first zone is not terminated (No), the live display data generator 3-6 adds 1 to n at Step S6-6 and returns to Step S6-3. Subsequently, at Step S6-5, the live display data generator 3-6 determines whether the first zone in FIG. 12 has been terminated, and the live display data generator 3-6 repeats the process from Step S6-3 to Step S6-6 until the termination (Yes). In this way, the difference data for live display $C_1$, $C_2$, $C_3$, $C_4$, . . . are obtained as in the lower diagram in FIG. 12. Causing the display 7 to sequentially display these difference data (the images for live display) ensures performing the live display (the real-time display) of the bodily fluid data. In this case, the difference data $C_1$ corresponds to the first frame, the difference data $C_2$ corresponds to the second frame, . . . the difference data $C_n$ corresponds to n-th frame in the live display.

At Step S6-5, when the first zone is terminated, the live display data generator 3-6 converts the live display data (the difference data) $C_1$ to $C_n$ stored in the data storage 5 into one moving image file (such as in an AVI format) and stores the moving image file in the data storage 5.

As described above, the live display data generator 3-6 ensures displaying an actual bodily fluid state (the leakage fluid state) on a real-time basis by performing arithmetic processing (for example, differential processing) on the first bodily fluid data (for example, the reference data) at the first timing (for example, the timing at $T_1$) and the second bodily fluid data at the second timing (for example, the timing at $T_2$, the timing at $T_3$) different from the first timing to generate the data for live display.

Since the difference between the bodily fluid data (the reference data) $B_1$ obtained first and the bodily fluid data $B_n$ obtained last is displayed live, the generation process according to the embodiment is less likely to be affected even when a position of an organ (tissues) varies in an interim progress. For example, in FIG. 12, when the difference data $C_1$ to $C_4$ are sequentially live-displayed as the first frame to the fourth frame of the live display, the difference data $C_4$ to be displayed last is generated based not on the bodily fluid data $B_3$ generated in the middle but on the bodily fluid data $B_5$ generated last even when the position of the organ largely varies at the timing when the bodily fluid data $B_3$ as a basis for the difference data $C_2$ is generated; therefore, the generation process according to the embodiment is less likely to be affected by the position variation of the organ in the interim progress.

The generation process according to the embodiment ensures reducing an effect (for example, a non-smooth moving image is displayed due to a positional deviation of the tissues between the plurality of images in the data for live display (the moving image)) caused by the position variation of the tissues in the bodily fluid data depending on an increase of n (an increase in a count of generation timing of the bodily fluid data) by a process taking the differences between the bodily fluid data generated nearly on a real-time basis at the respective timings and the reference data $B_1$ generated at the reference timing in the beginning of the live display. For example, when a relative position of the tissues that constitute an organ or the like of a human body slightly varies due to an external force, such as a respiration, there is a possibility of an occurrence of a slight positional deviation of the tissues between the plurality of generated images (between the plurality of pieces of bodily fluid data). For example, in FIG. 12, when the differential processing is performed between the bodily fluid data $B_1$ at the timing $T_1$ and the bodily fluid data $B_3$ at the timing $T_3$, the first generation process of the embodiment is not affected by the position variation that occurs between the reference timing of $T_1$ and the timing of $T_3$ (for example, at the timing of $T_2$), and there occurs only the position variation of the tissues at the timing of $T_3$ with respect to the timing of $T_1$; therefore, the first generation process of the embodiment ensures reducing an effect caused by the position variation of the tissues occurring between the images based on the generated respective bodily fluid data.

Second Generation Process Example

Next, a second generation process example according to the embodiment will be described. In the second generation process example, the live display data generator 3-6 obtains the difference data between the first bodily fluid data obtained at the first timing (for example, a timing of $T_{11}$) and the second bodily fluid data obtained at the timing after the predetermined time $\Delta t$ passes from the first timing (for example, a timing of $T_{12}$, a timing of $T_{13}$) to generate data for live display by an operation based on integral values obtained by sequentially integrating the difference data along elapse of time. It should be noted that the data generation for live display may use division data instead of the above-described difference data.

Figure 14:
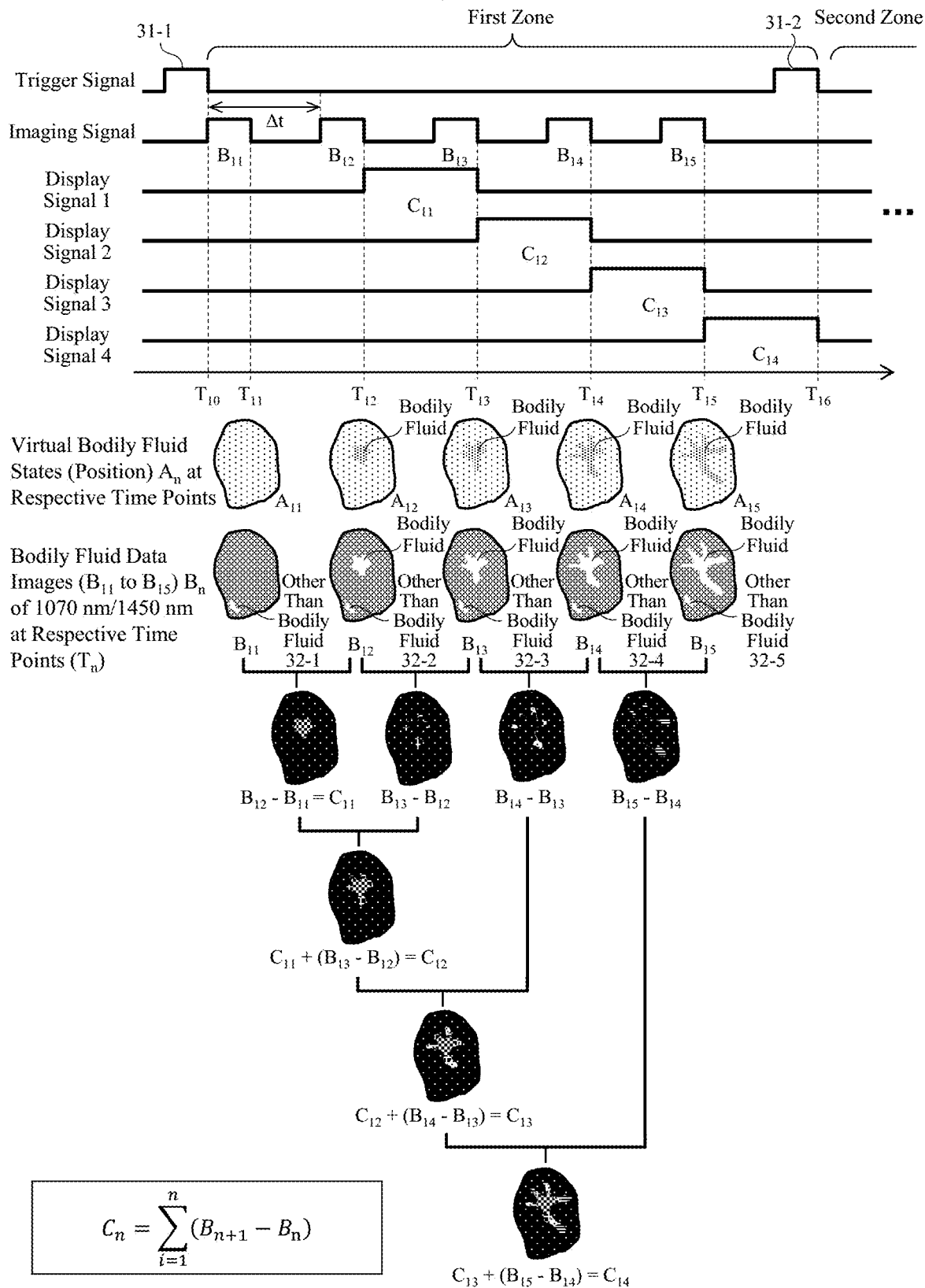
FIG. 14 includes a timing chart diagram (an upper diagram) illustrating output timings of images by imaging signals in a second generation process example and moving image data for live display, and a diagram (a lower diagram) illustrating images generated at the respective timings, according to the embodiment.

FIG. 14 includes a timing chart diagram (an upper diagram) illustrating output timings of images by imaging signals in the second generation process example and moving image data for live display and the diagram (the lower diagram) illustrating images generated at the respective timings. This timing chart diagram assumes a condition where the bodily fluid leaks at a time point of $T_{12}$ and the leaked bodily fluid expands on the tissues as the time passes.

Figure 15:
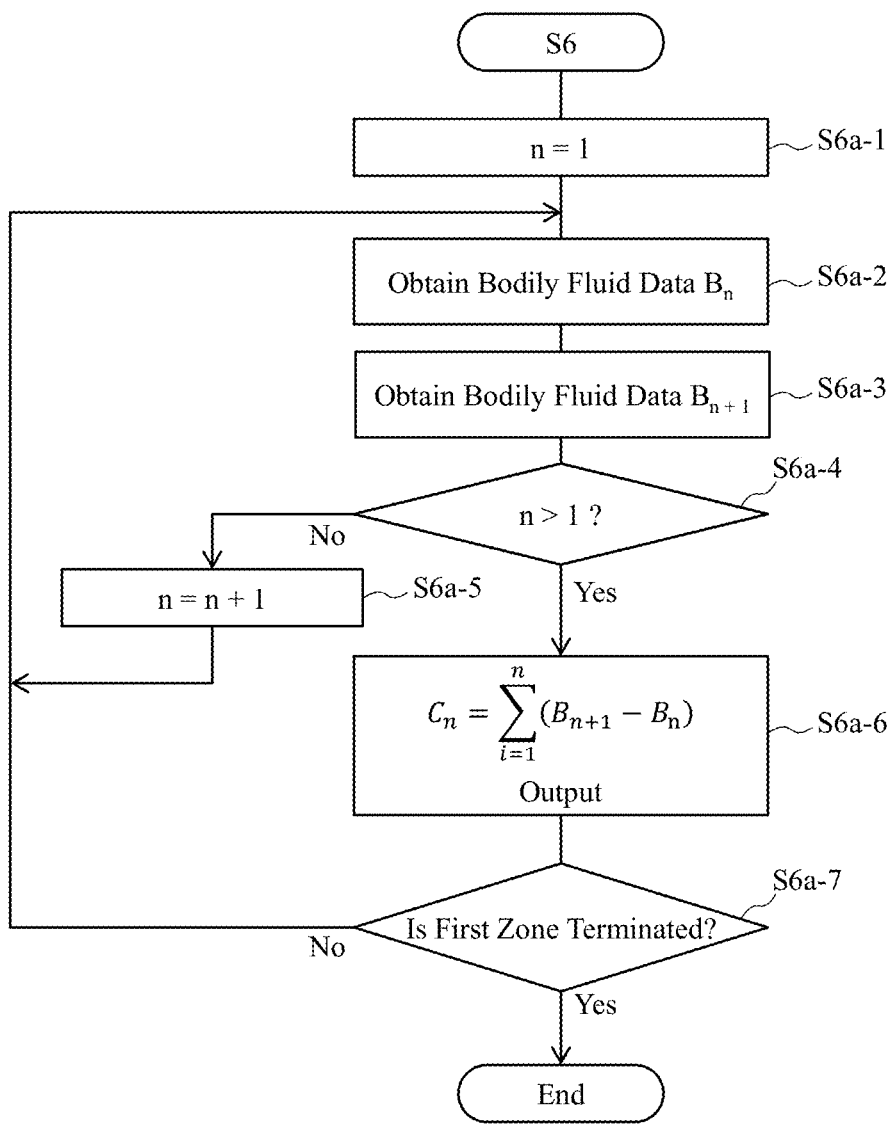
FIG. 15 is a flowchart diagram illustrating an exemplary procedure of a process in the second generation process example according to the embodiment.

FIG. 15 is a flowchart diagram illustrating an exemplary procedure of the process in the second generation process example. FIG. 15 illustrates a procedure of the process after generating the bodily fluid data (the comparison data) at Step S6 in FIG. 2A.

When the trigger signal (for example, a signal of a process start and a signal of a process termination) 31-1 illustrated in FIG. 14 is output, bodily fluid data at the timing $T_{11}$ is obtained as an image based on the imaging signal. At the timing $T_{11}$, while the bodily fluid is not leaked on the tissues, there is a case where a portion other than the bodily fluid is highlighted due to the absorption property even in the portion other than the bodily fluid, and this appears in the image of the bodily fluid data as a noise on the image. It should be noted that in images $B_n$ other than the image $B_{11}$, bodily fluid data and data other than the bodily fluid are illustrated.

It should be noted that FIG. 14 has an upper row (below the timing chart) where virtual bodily fluid states $A_n$ are illustrated in schematic diagrams.

Next, FIG. 15 will be described. First, at Step S6a-1, when the trigger signal is output by an operation of the input apparatus 6, the live display data generator 3-6 performs an initialization with n=1.

Next, at Step S6a-2, the live display data generator 3-6 obtains the bodily fluid data $B_n$, for example, the bodily fluid data $B_{11}$ at the timing of $T_{11}$ and temporarily stores the bodily fluid data $B_{11}$ in the data storage 5.

At Step S6a-3, the live display data generator 3-6 obtains the bodily fluid data $B_{n+1}$ at the timing of $T_{12}$ after $\Delta t$ passes from the timing of $T_{11}$, that is, bodily fluid data $B_{12}$, and temporarily stores the bodily fluid data $B_{12}$ in the data storage 5.

The live display data generator 3-6 determines whether n>1 or not at Step S6a-4, and when it is No, the procedure proceeds to Step S6a-5 such that the live display data generator 3-6 increments n by 1. Then, the procedure returns to Step S6a-2.

When n>1, the live display data generator 3-6 obtains an integral value $C_n$ of the difference data $B_{n+1}-B_n$ by the following Formula (2) at Step S6a-6.

[Formula 2]

$$C_n = \Sigma_{i=1}^{n}(B_{n+1}-B_n) \qquad (2)$$

Then, the live display data generator 3-6 sequentially outputs the integral value $C_n$ to the display 7 along elapse of time.

Subsequently, at Step S6a-7, the live display data generator 3-6 determines whether the first zone in FIG. 14 has been terminated, that is, whether the trigger signal 31-2 that instructs a termination of the live display of the leakage fluid has been output. The live display data generator 3-6 repeating the process from Step S6a-2 to Step S6a-6 until the termination (Yes) from the start ensures obtaining the difference data $C_{11}=B_{12}-B_{11}, C_{12}, C_{13}, C_{14}, \ldots$ as in four rows in the lower diagram in FIG. 14. As indicated in the above-described Formula (2), the live display data generator 3-6 sequentially integrates (adds) these difference data $C_{11}, C_{12}, C_{13}, C_{14}, \ldots$ with elapse of time and causes the display 7 to sequentially display the integral values, thus ensuring performing the live display (the real-time display) of the bodily fluid data. In this case, the difference data $C_{11}$ corresponds to a first frame in the data for live display, the difference data $C_{12}$ corresponds to a second frame in the data for live display, ... the difference data $C_n$ corresponds to n-th frame in the data for live display.

At Step S6a-7, when the first zone is terminated, the live display data generator 3-6 converts the live display data (the difference data) $C_{ii}$ to $C_n$ stored in the data storage 5 into one moving image file (such as in an AVI format) and stores the moving image file in the data storage 5.

As described above, the live display data generator 3-6 performs the arithmetic processing (for example, the differential processing) on the first bodily fluid data $B_n$ obtained at the first timing and the second bodily fluid data $B_{n+1}$ obtained at the second timing after the predetermined time $\Delta t$ passes from the first timing to obtain the difference data $C_n$. Then, the live display data generator 3-6 ensures displaying an actual bodily fluid state (the leakage fluid state) on a real-time basis by generating the data for live display based on the integral values obtained by sequentially adding the difference data along the elapse of leakage time or photographing time to generate the data for live display based on the generated data.

It should be noted that, in the above-described first generation process example and second generation process example, the image $C_n$ (for example, $C_1$, $C_2$, $C_{11}$) generated by the arithmetic processing (for example, the subtraction, the division) may be configured to be obtained from the real-time comparison data generator 3-5 (FIG. 1C) in the above-described second embodiment. In this case, the live display data generator 3-6 according to this embodiment causes the display 7 to sequentially display the image $C_n$ (for example, $C_1$, $C_2$, $C_{11}$) obtained from the real-time comparison data generator 3-5 to generate the live display data.

(Noise Removal Process)

As described above, in the first and the second generation process examples, in order to remove a portion other than the bodily fluid (the noise region) 32-$n$, the live display data generator 3-6 takes differences between the bodily fluid data $B_n$ generated at different timings to cancel (remove, hide) the noise region 32-$n$. However, for example, when the relative position of the organ (the tissues) largely varies at one timing, the position of the noise region varies in association with the variation; therefore, there is a case where the positions of the noise region 32-$n$ on the data (the images) do not match even after the differences (or the divisions) between the bodily fluid data $B_n$ are taken, thus being incapable of removing the noise region 32-$n$.

Therefore, in this embodiment, as illustrated in FIG. 11A, a noise region remover 6b that hides or removes the noise region 32-$n$ other than the display region based on the bodily fluid data $B_n$ is disposed in the input apparatus 6. The noise region 32-$n$ includes a non-highlighted region where a highlight is not desired or non-display is desired in the image to be displayed.

For example, the noise region remover 6b includes all or a part of the following functions.

1) The noise region remover 6b calculates a temporal amount of movement (amount of variation) of the organ in a screen by detecting a marker (such as a two-dimensional pattern and a reflective marker) attached on a surface of the organ (the tissues) in advance with an optical sensor and tracking the position of the marker. Then, the noise region remover 6b shifts the bodily fluid data before the movement or after the movement of the organ in a planar surface of the image based on the amount of movement of the organ to match the positions of the noise regions of the bodily fluid data between which a difference is obtained, thus removing the noise region.

2) The noise region remover 6b causes a timing of photographing to be in synchronization with a rhythm (a cycle) of a respiration of an inspection target (a patient). Since the patient respires during a surgery, there is a case where the organ (the tissues) moves based on the cycle of respiration. In this case, there is a possibility that the region other than the bodily fluid (the noise region) cannot be removed even though the differential processing described above is performed. Therefore, the noise region remover 6b controls the imaging timing to match with the respiration timing, such as any one of inhale and exhale. In this case, the cycle of respiration of the patient may be detected by attaching a marker on the organ surface or the like in advance and tracking this marker, similarly to the above-described 1). This ensures the noise region remover 6b more effectively removing the noise.

3) The noise region remover 6b may be configured to remove the region instructed by the input apparatus 6 as image processing. For example, the noise region remover 6b may remove the noise region 32-$n$ by detecting a shape of the region in a periphery of a point instructed by the input apparatus 6 and tracking the region of the detected shape, as well as replacing a luminance value of a pixel in the shape with an average luminance value of the pixel outside the shape. In this case, the noise region remover 6b may prevent the difference data $C_n$ from being generated and cause the display 7 to directly live-display the bodily fluid data $B_n$ and then, remove the noise region with respect to the bodily fluid data $B_n$.

4) Alternatively, in the first generation process, the data generator 3 (or the live display data generator 3-6) may terminate the first zone when the organ (the tissues) largely changes during the first zone to start the second zone in a state after the organ changes. In this way, the above-described reference image is newly obtained again (reset). Accordingly, the positions of the noise region 32-$n$ of the reference image and the bodily fluid data after an elapse of the predetermined time mutually match, thereby ensuring a removal of the noise region. In this case, the noise region remover 6b may detect the position of the noise region (the position of a portion other than the bodily fluid) in the reference image and the position of the noise region 32-$n$ of the bodily fluid data $B_n$ of the differential target, and start the second zone when the positions of the two changes by a predetermined value or more.

(Leakage Source Analyzer)

The live display data generator 3-6 includes the outflow source analyzer 3-6a that estimates a source of leakage of the bodily fluid in the tissues to specify a position of the source of leakage.

The outflow source analyzer 3-6a stores the data for live display (the moving image data) generated in the above-described first or second generation process as storage data in the data storage 5. The outflow source analyzer 3-6a tracks the data in a temporarily opposite direction based on these storage data to estimate and obtain the position of the source of leakage by rewinding back to the start of leakage and interpolating to zero hours. The outflow source analyzer 3-6a may calculate an area of the leakage fluid (the leaked-out bodily fluid) in the image and a center of gravity of the area using the data for live display (for example, the image $C_2$, the image $C_{12}$) generated in the above-described first or second generation process to estimate and calculate the position of the source of leakage based on the center of gravity of the area and a direction in which the leakage fluid expands (for example, a direction in which the leakage fluid flows with the center of gravity as a point of origin). For example, the outflow source analyzer 3-6a may add information indicative of the position of the source of leakage to the data for live display (for example, the image $C_2$, the image $C_{12}$) based on the specified source of leakage described above and display the position of the source of leakage with a mark or the like on the display image of the display 7 (for example, display a mark indicative of the source of leakage overlapped on the display image). A user, such as a doctor, can conduct a treatment (for example, a treatment to stop a leakage fluid using an instrument or the like) for the leakage fluid leaking on the tissue surface while viewing the source of leakage on this displayed image.

It should be noted that the controller 3A in the embodiment includes a mode to display a moving image and includes a function to switch the moving image display mode and a still image display mode.

Fourth Embodiment

In the above-described process (the second embodiment), the observation apparatus A obtains the data (the bodily fluid data) before the passage of T hours and after the passage of T hours at the predetermined time interval or any time interval, and compares the two, thus ensuring highlighting the bodily fluid. A time after the passage of T hours may be the timing at which, for example, the observer visually observes the bodily fluid flowing out.

In the embodiment, a data change detector 3-5a is disposed as illustrated in Step S5-2 in FIG. 1C and FIG. 2B. When data changes at a certain timing, the data at that timing and data T hours before, which is stored in the storage (for example, a buffer memory) or the like of the observation apparatus A, are compared.

In this way, by the image processing automatically detecting a change in an image, there is an advantage that the arithmetic processing by the comparison calculator 3-3 is only necessary to be performed only at the timing of the change. The data change detector 3-5a automatically obtaining the timing when the data largely changes ensures highlighting only the bodily fluid data even when the observation is not conducted all the time, similarly to the second embodiment.

Fifth Embodiment

Next, a description will be given of another embodiment using the observation apparatus A and the observation system 100. For example, since the main component of the bodily fluid is water, the observation system 100 according to the embodiment uses the wavelength of 1070 nm±50 nm (small absorptance of light) within a region of the first infrared wavelength, which is a distinctive wavelength of a water, and the wavelength of 1450 nm±50 nm (large absorptance of light) within a region of the second infrared wavelength and performs a comparison (operation), such as the difference and the division, on the two, thus ensuring highlightedly displaying the bodily fluid on the tissue surface.

However, for example, in a laparotomy for a liver, there is a case where two types of bodily fluids of a bile and a blood simultaneously leak out on a surface of the tissues 11. Therefore, generating a highlighted image using the wavelength of 1070 nm and the wavelength of 1450 nm possibly highlights both bodily fluids of the bile and the blood, thus making it difficult to determine the two (FIGS. 16(a), (b)).

Figure 17:
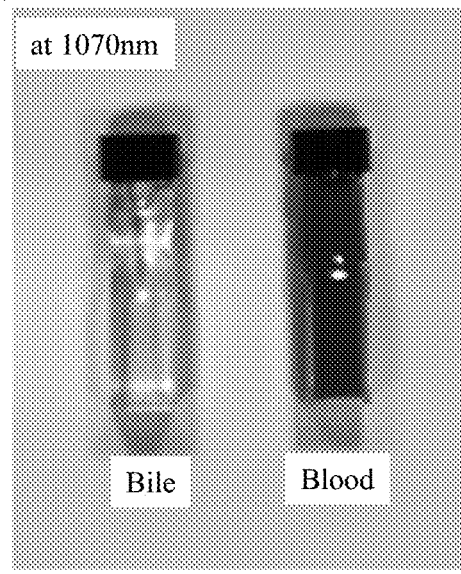
FIG. 17($a$) is an exemplary image of a measurement with the wavelength of 1070 nm where a bile derived from a pig and a blood derived from the pig are put in quartz cells (cuvettes).
Figure 17:
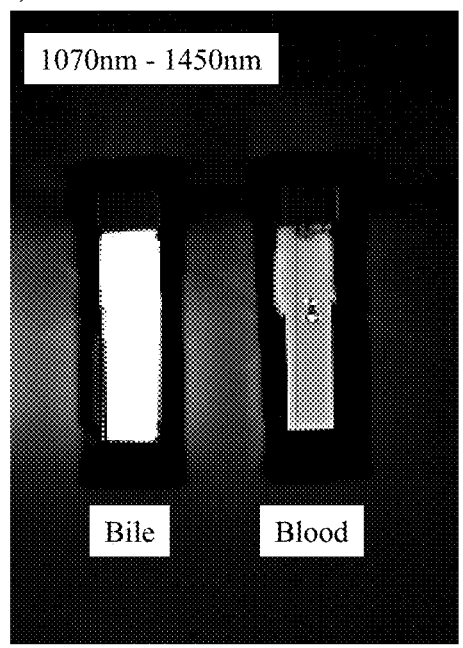
Figure 17:
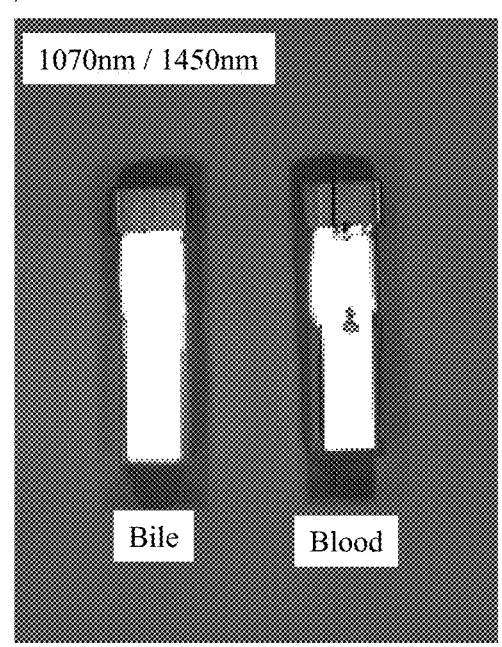

FIG. 17(a) is an image where a bile derived from a pig and a blood derived from the pig are put in quartz cells (cuvettes) and measured with the wavelength of 1070 nm.

As illustrated in FIG. 17(b) and FIG. 17(c), there is a problem where while the bile is highlighted, the blood is also highlighted when the arithmetic processing of 1070 nm-1450 nm and 1070 nm/1450 nm are performed.

Figure 18:
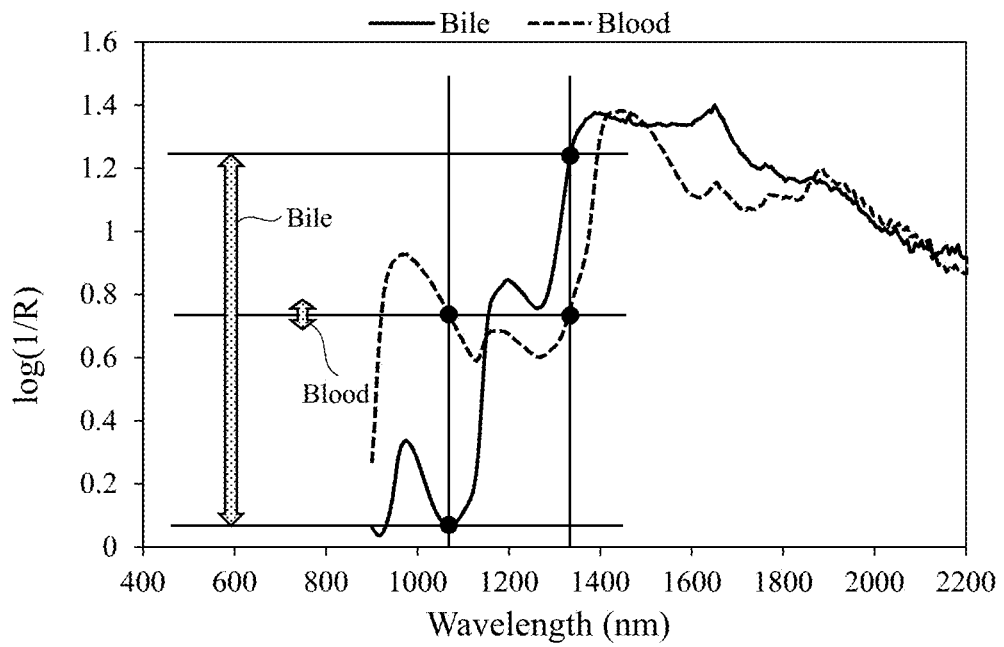
FIG. 18 is a diagram illustrating exemplary wavelength dependences of reflectivities when a highlighted image of the bile and the blood is generated using the wavelengths of 1070 nm and 1330 nm according to the embodiment and a diagram that corresponds to FIG. 16($b$).

Then, as illustrated in FIG. 18, the comparison calculator 3-3 performs the comparison operation (such as subtracting (differential), dividing processing) on two pieces of data with different wavelengths of, for example, 1070 nm±50 nm (a first wavelength) and 1330 nm±50 nm (a second wavelength) that hardly have a difference in reflectivity in blood and have a large difference in reflectivity in bile, set by the wavelength band setting apparatus 3-4. This ensures highlightedly displaying only the bile on the display 7.

Figure 19:
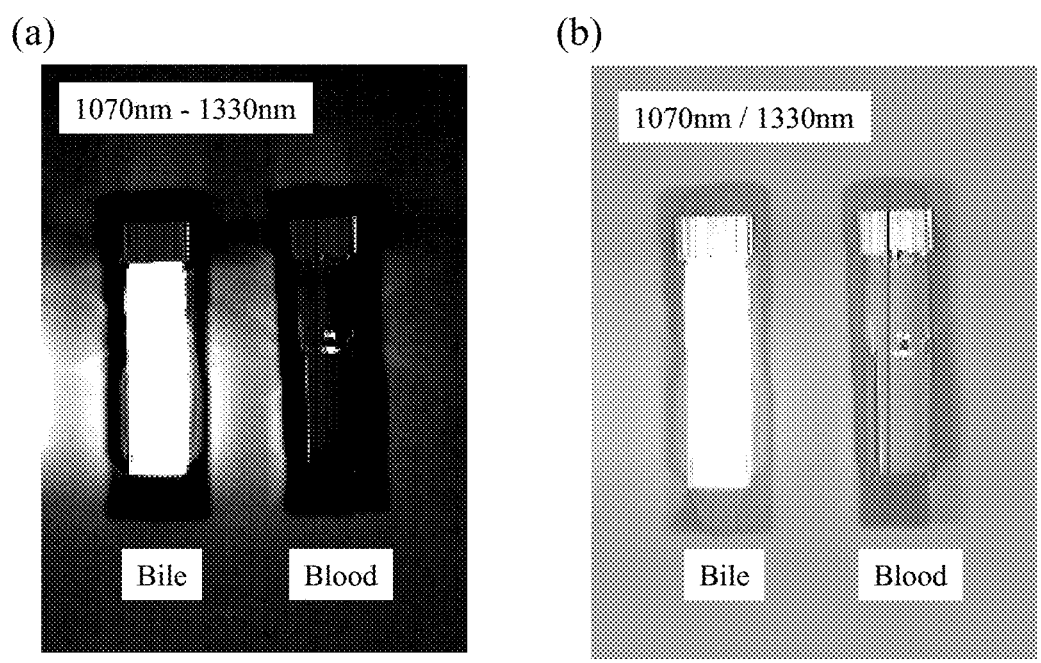
FIG. 19 includes diagrams illustrating exemplary images obtained with a condition in FIG. 18.
Figure 20A:
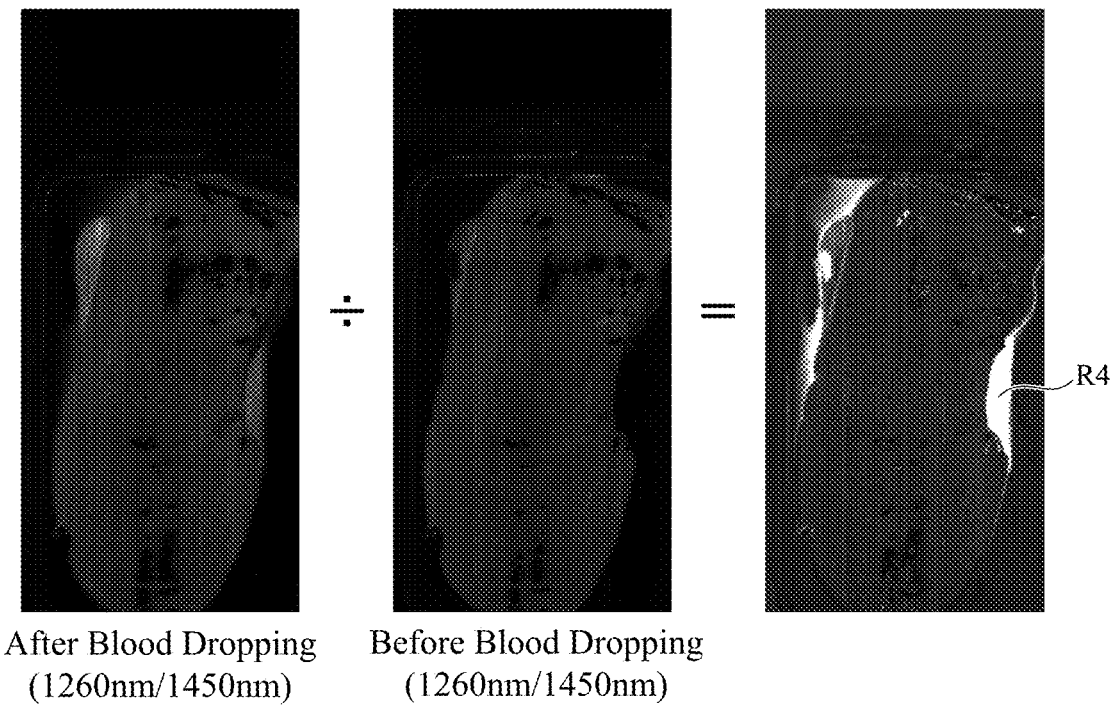
FIG. 20A is a diagram illustrating exemplary images obtained by arithmetic processing for highlight processing of blood according to the embodiment.
Figure 20B:
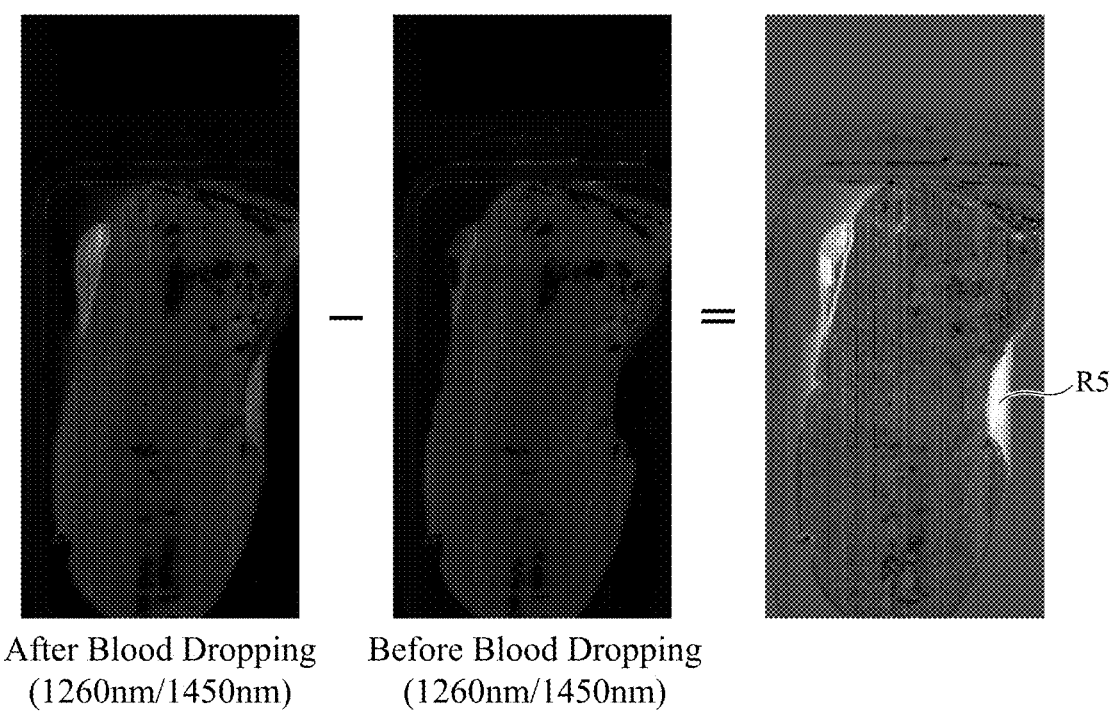
FIG. 20B is a diagram illustrating exemplary images obtained by arithmetic processing for highlight processing of blood according to the embodiment.
Figure 20C:
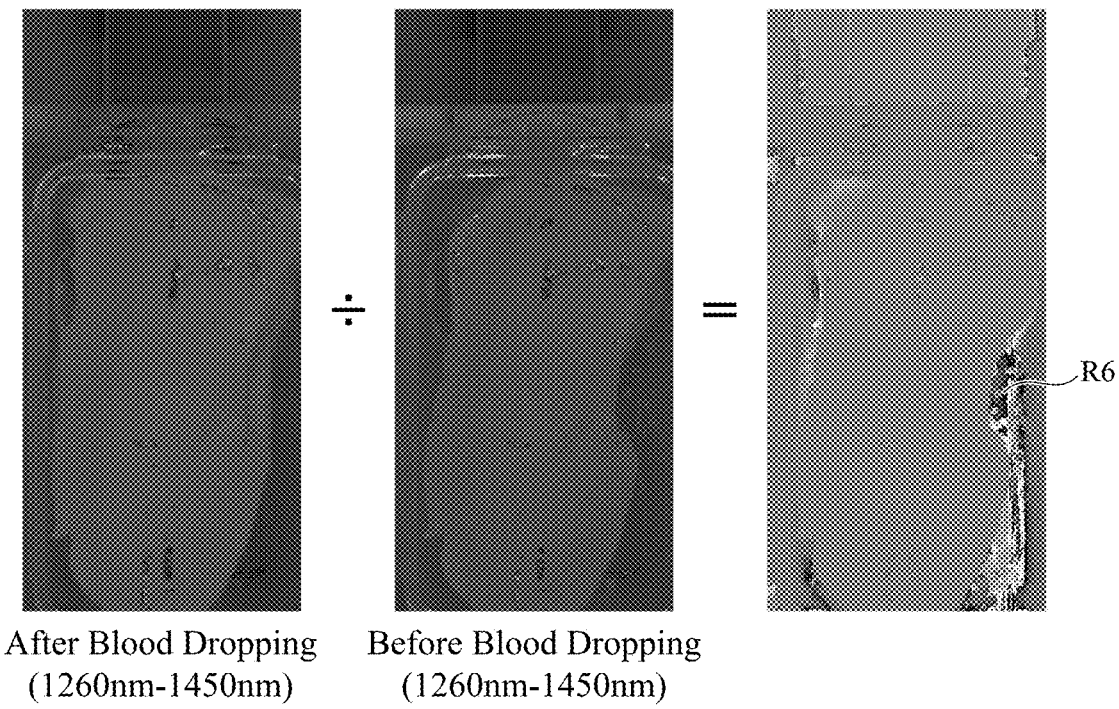
FIG. 20C is a diagram illustrating exemplary images obtained by arithmetic processing for highlight processing of blood according to the embodiment.
Figure 20D:
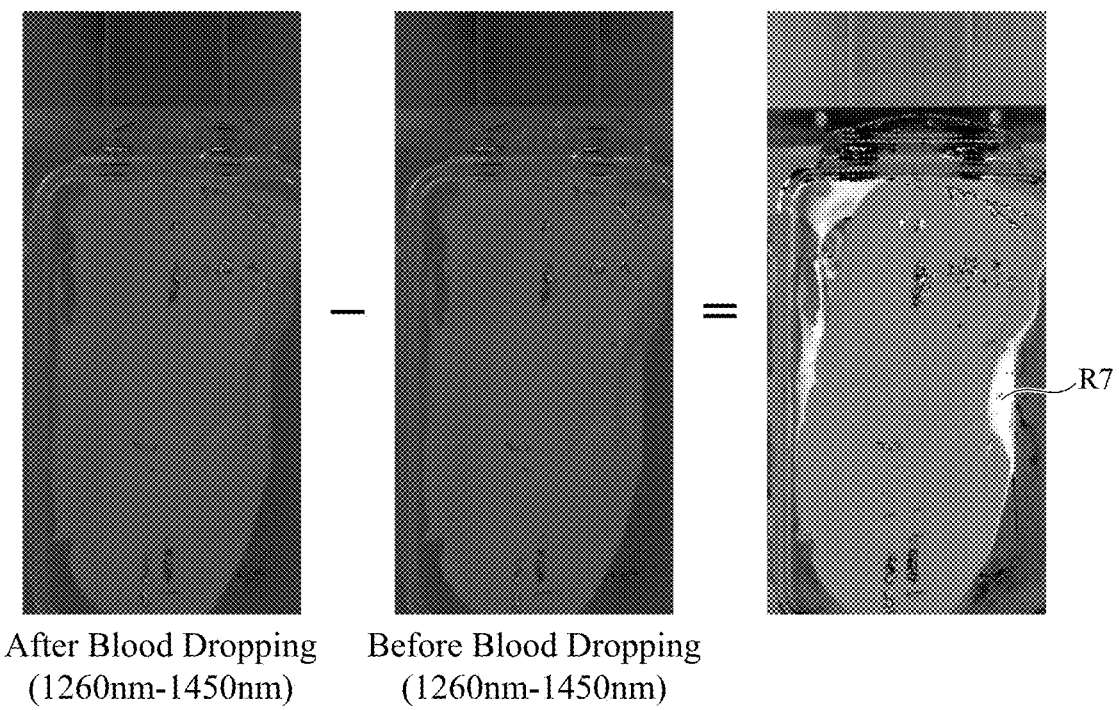
FIG. 20D is a diagram illustrating exemplary images obtained by arithmetic processing for highlight processing of blood according to the embodiment.

As illustrated in FIGS. 19(a), (b), the observation system 100 ensures highlighting only the bile, thereby ensuring extracting an image of the bile with a reduced effect of the blood.

In the above-described example, while an example that uses, for example, 1330 nm as the second infrared wavelength region of the second infrared light has been described, the observation system 100 can use the infrared light in a wavelength band from 1250 nm±50 nm to 1400 nm±50 nm and separately highlight the bile from the blood (highlightedly displaying only the bile).

Figure 16:
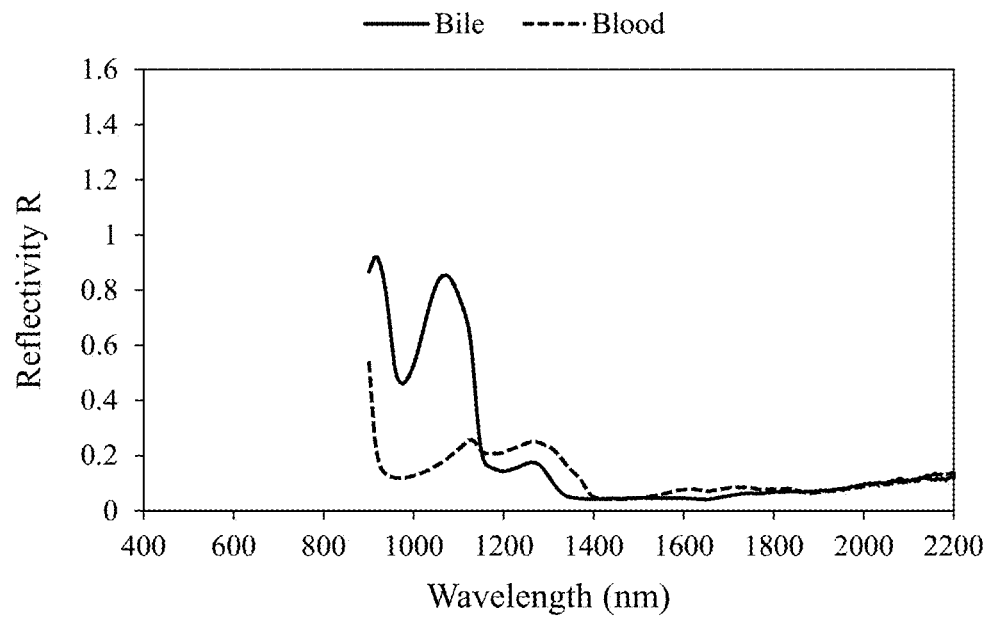
FIG. 16($a$) is a diagram illustrating exemplary wavelength dependences of reflectivities of a bile and a blood when a highlighted image is generated using infrared lights with a wavelength of 1070 nm and a wavelength of 1450 nm.
Figure 16:
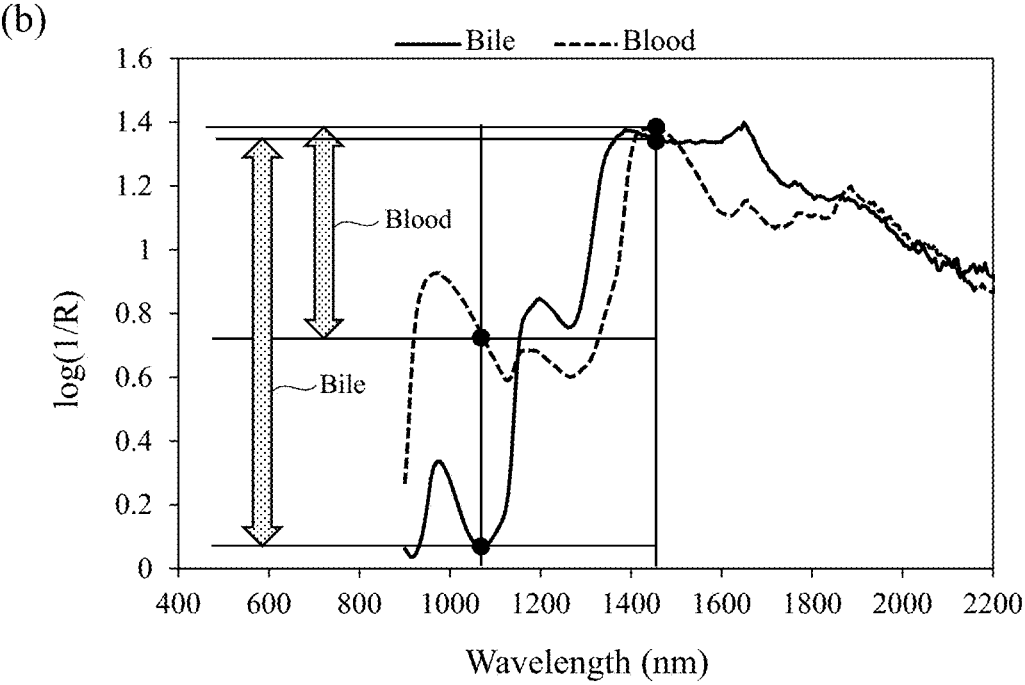

It should be noted that, while the above-described description has described an example of a case where the bile is a target to be highlighted on the surface of the tissues 11, considering a relationship between the wavelength and the optical property as illustrated in FIG. 16(a), FIG. 16(b) ensures obtaining a preferred wavelength (bandwidth) also when other bodily fluids are desired to be highlighted.

As described above, in the embodiment, the observation system 100 can highlight and display the bile out of the bile and the blood on the image. Accordingly, even though a blood flows out together with the bile during an actual surgery or the like, there is an advantage that only the bile can be highlighted.

While the embodiment in which the bile is highlighted has been described above, FIG. 20A to FIG. 20D are diagrams illustrating an embodiment in which a blood is highlighted by operations of data obtained at different timings (timings before and after a predetermined time passes, such as before a blood dropping and after a blood dropping) similarly to the case of the bile in the real-time comparison data generator 3-5.

The following describes the respective arithmetic processing.

1) FIG. 20A:

Data after blood dropping: data obtained by dividing first data with the wavelength of 1260 nm of the infrared light by second data with the wavelength of 1450 nm.

Data before blood dropping: data obtained by dividing the first data with the wavelength of 1260 nm of the infrared light by the second data with the wavelength of 1450 nm.

The data on the right side obtained by dividing the data after blood dropping by the data before blood dropping reflects a distribution of the blood accumulated on a bottom of a container where a liver is placed as indicated by a region R4.

2) FIG. 20B:

Data after blood dropping: data obtained by dividing the first data with the wavelength of 1260 nm of the infrared light by the second data with the wavelength of 1450 nm.

Data before blood dropping: data obtained by dividing the first data with the wavelength of 1260 nm of the infrared light by the second data with the wavelength of 1450 nm.

The data on the right side obtained by subtracting the data before blood dropping from the data after blood dropping reflects a distribution of the blood accumulated on a bottom of a container where a liver is placed as indicated by a region R5.

3) FIG. 20C:

Data after blood dropping: data obtained by subtracting the second data with the wavelength of 1450 nm from the first data with the wavelength of 1260 nm of the infrared light.

Data before blood dropping: data obtained by subtracting the second data with the wavelength of 1450 nm from the first data with the wavelength of 1260 nm of the infrared light.

The data on the right side obtained by dividing the data after blood dropping by the data before blood dropping reflects a distribution of the blood accumulated on a bottom of a container where a liver is placed as indicated by a region R6.

4) FIG. 20D:

Data after blood dropping: data obtained by subtracting the second data with the wavelength of 1450 nm from the first data with the wavelength of 1260 nm of the infrared light.

Data before blood dropping: data obtained by subtracting the second data with the wavelength of 1450 nm from the first data with the wavelength of 1260 nm of the infrared light.

The data on the right side obtained by subtracting the data after bile dropping from the data after blood dropping reflects a distribution of the blood accumulated on a bottom of a container where a liver is placed as indicated by a region R7.

As described above, the blood can be highlighted by obtaining the data before the passage of T hours and after the passage of T hours at the predetermined time interval or any time interval and comparing the two. A time after the passage of T hours may be the timing at which, for example, the observer visually observes the blood flowing out.

As described above, with each of the above-described embodiments, the observation apparatus or the observation system of the embodiments ensures distinguishing the bodily fluids from other biological information among biological information flown out or adhered to the biological surface. The observation apparatus or the observation system of the embodiments ensures determining the bodily fluid out of the bodily fluids and other biological information on the biological surface.

Sixth Embodiment

Next, a description will be given of a sixth embodiment. An observation apparatus according to the embodiment relates to an observation technique that can clearly observe a surface of an organism (for example, a biological surface) without being affected by a regular reflection light from a bodily fluid flown out on the surface of the organism (for example, the biological surface) and spectral characteristics belonging to the bodily fluid itself using the observation technique of the bodily fluid distribution according to each of the above-described first to fifth embodiments.

Figure 21:
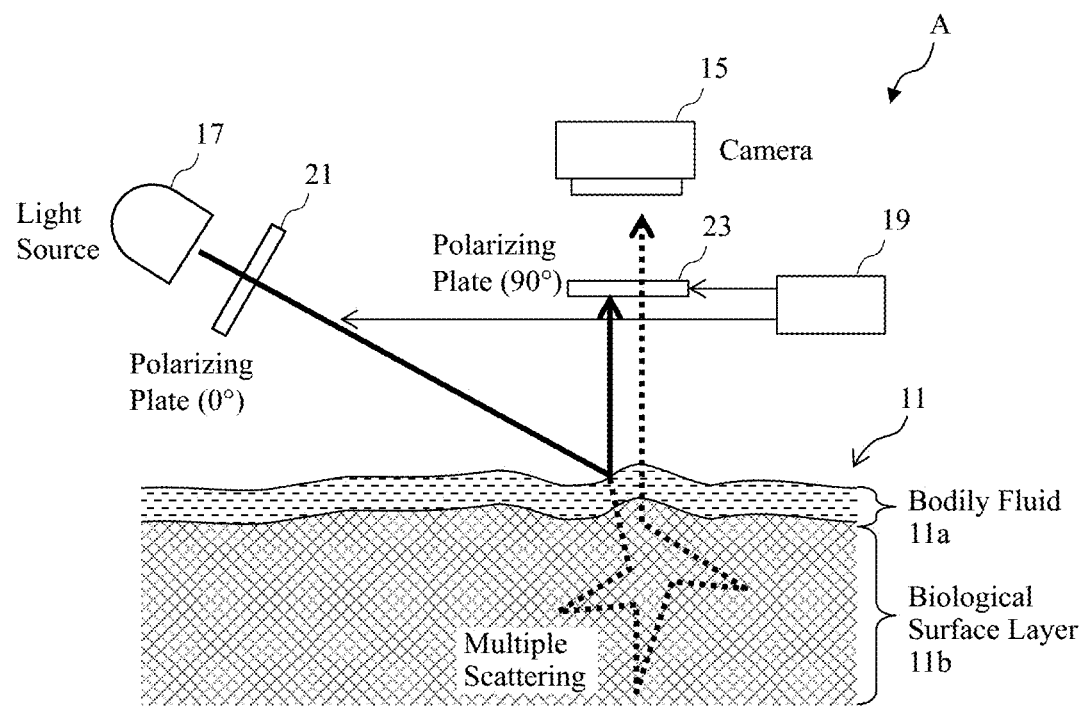
FIG. 21 is a diagram illustrating an exemplary principle of a biological surface observation technique according to the embodiment.

FIG. 21 is a diagram illustrating a principle of a biological surface observation and the configuration of the apparatus itself is similar to that illustrated in FIG. 1A. Here, the polarizing plate 21 and a polarizing plate 23 are used as one example. It should be noted that the switch 19 will be described in the sixth embodiment.

Disposing the polarizing plates 21 and 23 in a crossed-Nicol manner (a relationship where polarizing angles on a side of the light source 17 and a side of the camera 15 are shifted by 90°) ensures cutting the regular reflection light (an arrow with a solid line), which interferes with an observation of the biological surface (a surface of the tissues 11 of the organism). Accordingly, a scattered light (a dashed line) in which information of a biological surface layer existing beneath the bodily fluid is further reflected can be effectively detected. The stage 10 on which the tissues 11 are placed in FIG. 1A is configured to move relatively with respect to the imaging apparatus 15 and scan the tissues 11 in an XY plane (a surface perpendicular to a paper surface) when a dispersing typed hyperspectral camera is used as the imaging apparatus 15. It is preferred to configure the stage 10 to be able to move in a Z direction (a direction perpendicular to the XY plane). This, however, should not be construed in a limiting sense, and using LEDs having a plurality of wavelengths as the light source 17 ensures using a non-dispersed typed camera as the imaging apparatus 15. In this case, the stage 10 does not necessarily move relatively with respect to the imaging apparatus 15.

Figure 22:
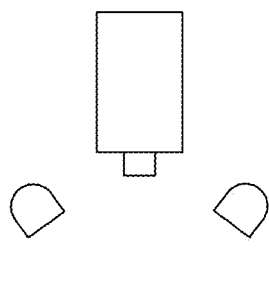
FIG. 22 includes diagrams illustrating examples of four configurations (from (b) to (e)) that are distinguished by an s polarization (a polarization perpendicular to an incidence plane), a p polarization (a polarization parallel to the incidence plane), and whether an arrangement of two polarizing plates in optical paths is vertical (crossed-Nicol) or horizontal (parallel), and a state without the polarizing plate ((a)) in an apparatus illustrated in FIG. 21.
Figure 22:
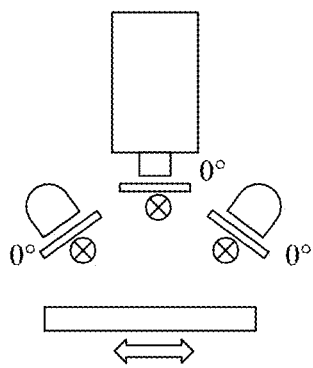
Figure 22:
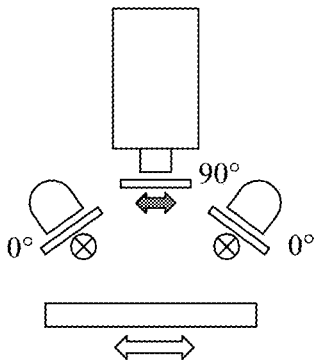
Figure 22:
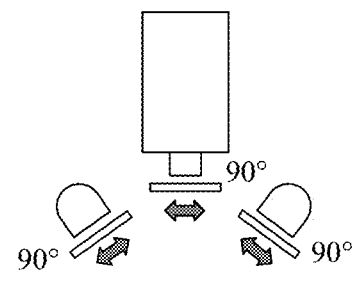
Figure 22:
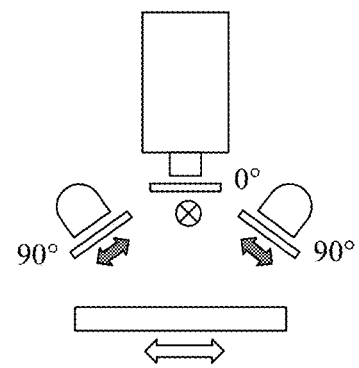

FIG. 22 includes diagrams illustrating four configurations (from (b) to (e)) that are distinguished by an s polarization (a polarization perpendicular to an incidence plane), a p polarization (a polarization parallel to the incidence plane), and whether an arrangement of the two polarizing plates in optical paths is vertical (crossed-Nicol) or horizontal (parallel), and a state without the polarizing plate ((a)) in an apparatus illustrated in FIG. 21.

FIGS. 23(a) to (e) are diagrams illustrating observation images of the biological surface measured with the configurations from FIGS. 22(a) to (e). However, FIG. 23(f) is a visible light image.

Figure 23:
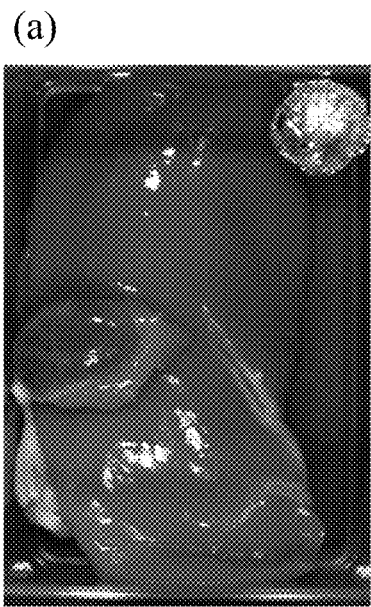
FIGS. 23($a$) to ($f$) are diagrams illustrating exemplary observation images of the biological surface measured with the configurations in FIG. 22($a$) to ($e$). However, FIG. 23($f$) is a diagram illustrating an exemplary visible light image.
Figure 23:
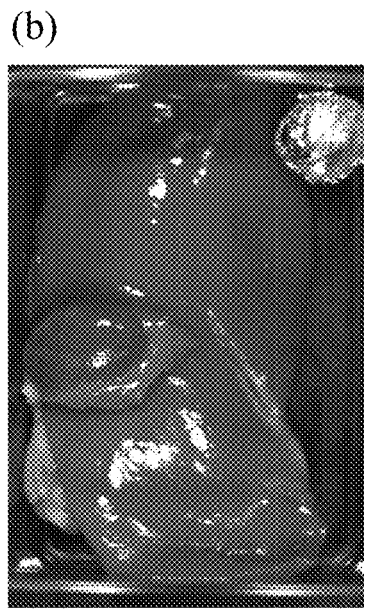
Figure 23:
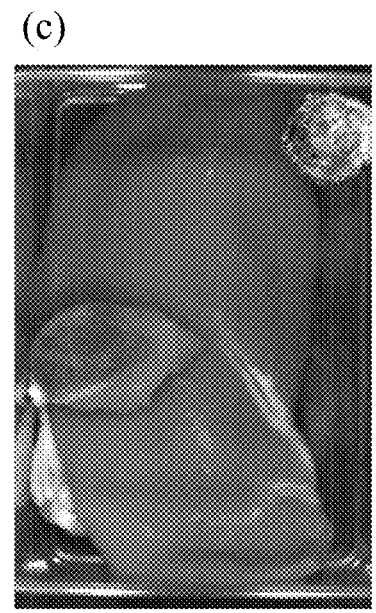
Figure 23:
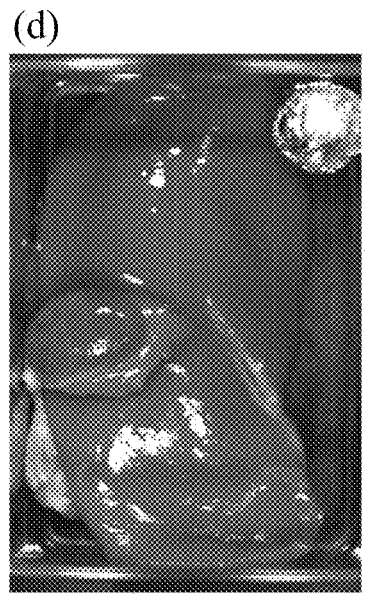
Figure 23:
Figure 23:
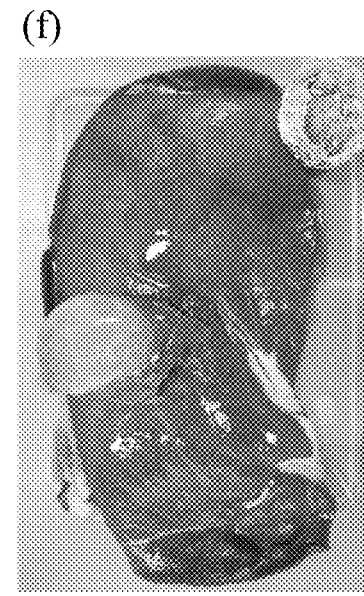

As can be seen from these diagrams, in FIGS. 23(c) and (e) with the crossed-Nicol, it is seen that the effect of the regular reflection light can be reduced unlike the other images.

Figure 24:
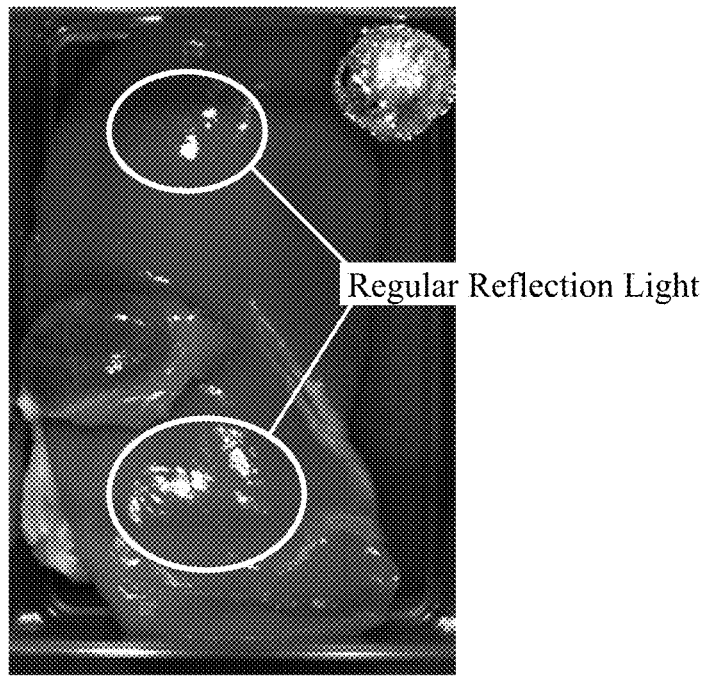
FIG. 24($a$) is an exemplary image without the polarizing plate in FIG. 23($a$) with the infrared light with the wavelength of 1070 nm whose absorptance of a water is small.
Figure 24:
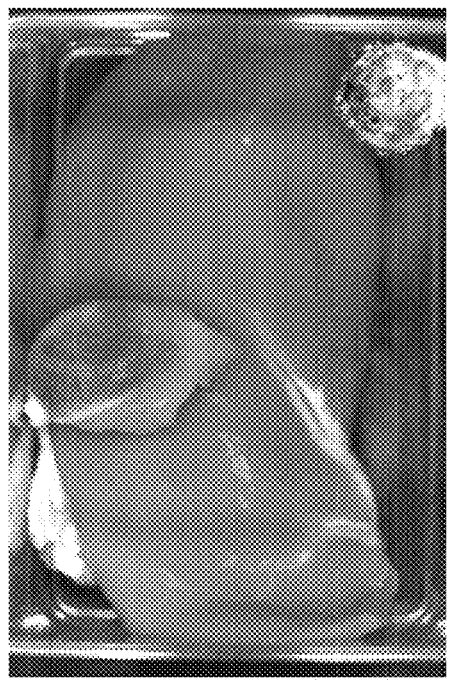

FIG. 24(a) is an image without the polarizing plate in FIG. 23(a) with the infrared light with the wavelength of 1070 nm whose absorptance of a water is small. FIG. 24(b) is an s polarization crossed-Nicol image in FIG. 23(c) with the wavelength of 1070 nm. As is clear from FIG. 24, with the crossed-Nicol, it is seen that the effect of the regular reflection light by the bodily fluid can be effectively reduced and an accurate observation of the biological surface is possible.

Figure 25:
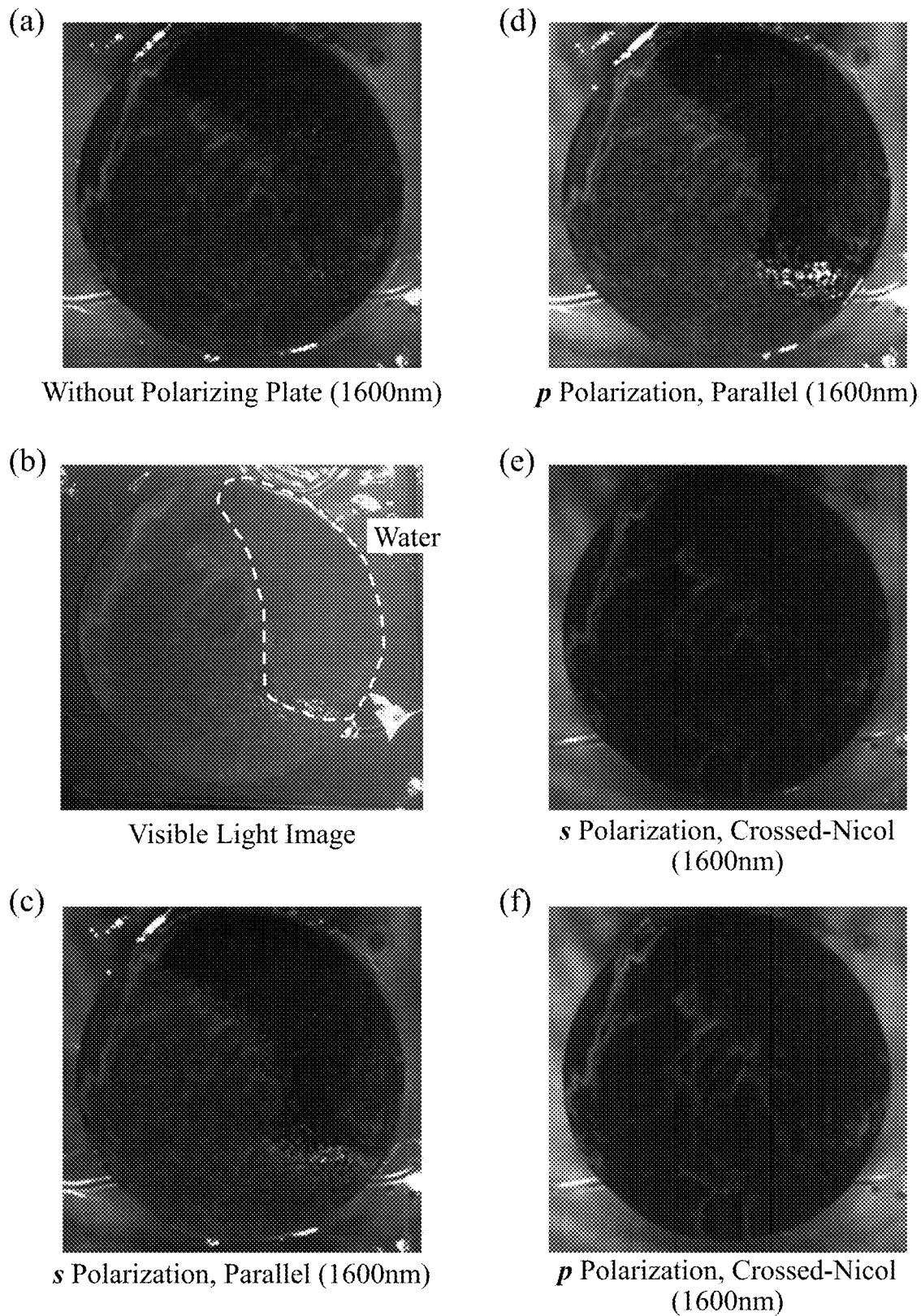
FIG. 25 includes diagrams illustrating exemplary results of observing a surface of a ham spuriously representing the biological surface with the respective configurations illustrated in FIG. 22.
Figure 26:
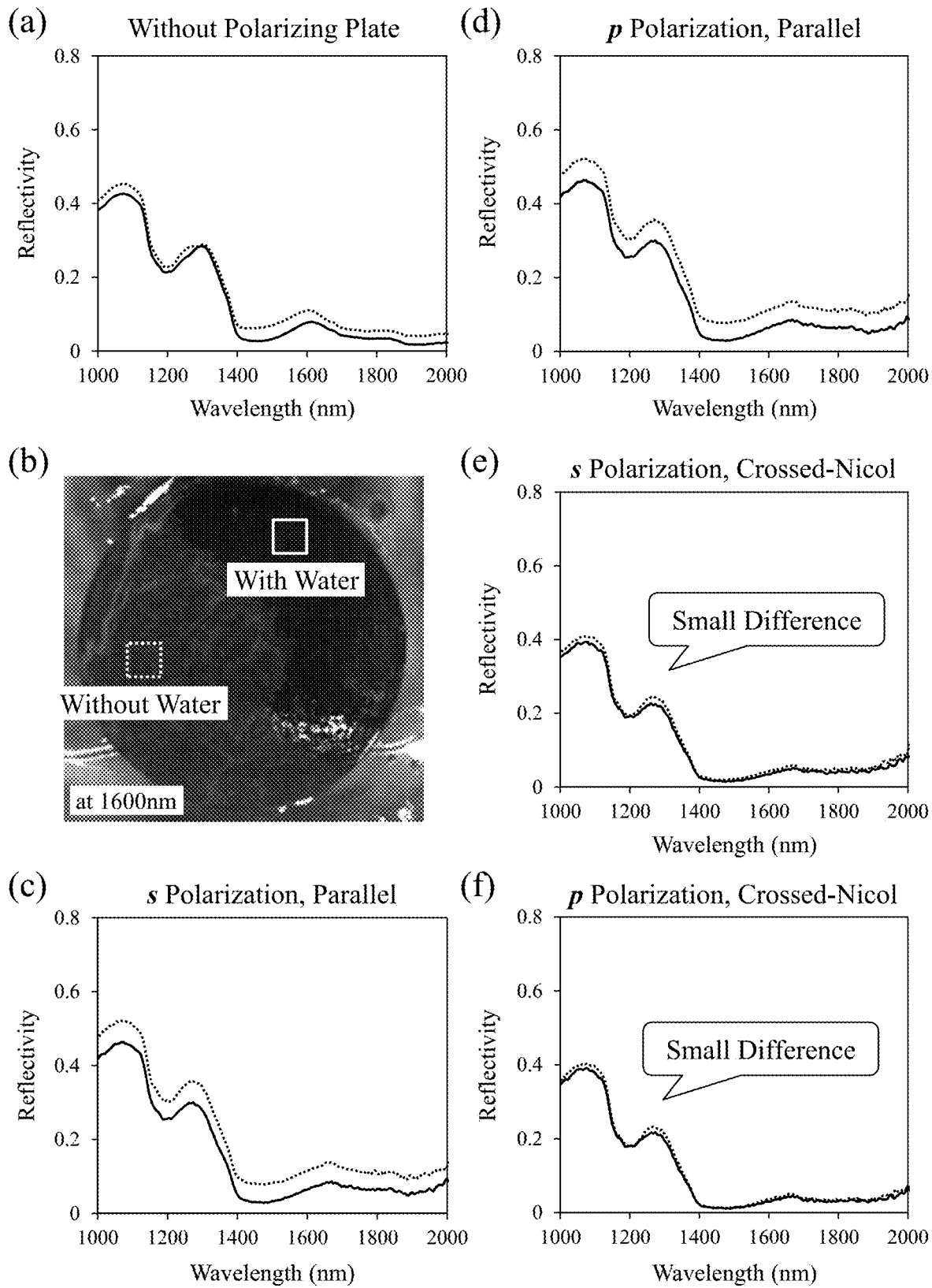
FIG. 26 includes diagrams illustrating exemplary wavelength dependences of reflectivities in respective optical configurations illustrated in association with the images illustrated in FIG. 25, and diagrams illustrating exemplary characteristics distinguished by presence or absence of a water. However, FIG. 26($b$) is an exemplary surface image observed at a wavelength of 1600 nm.
Figure 27:
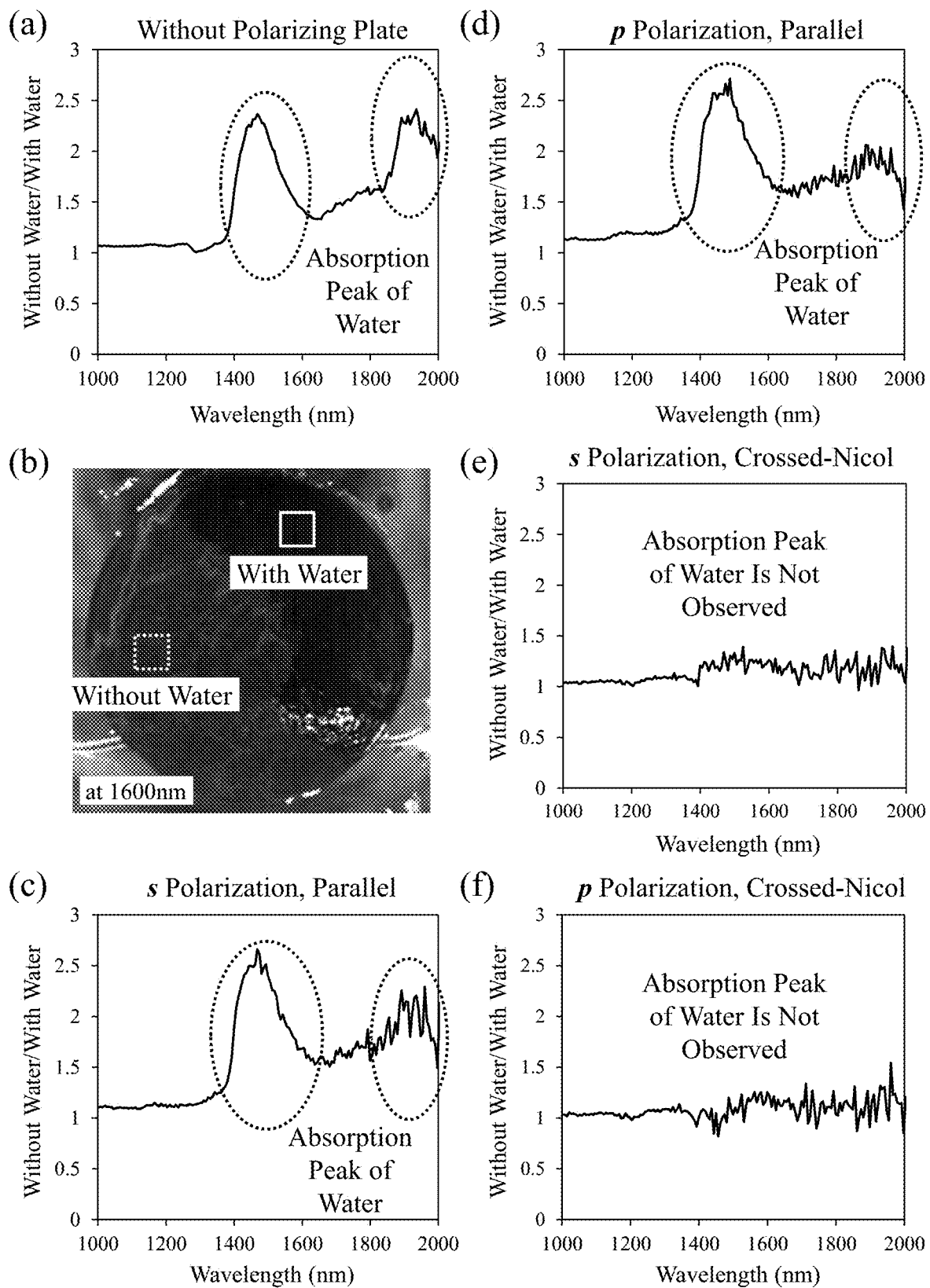
FIG. 27 includes diagrams illustrating exemplary wavelength dependences of values of (reflectivity without a water/reflectivity with a water) in the respective optical configurations illustrated in association with the images illustrated in FIG. 25. However, FIG. 27($b$) is an exemplary surface image observed at the wavelength of 1600 nm.

FIG. 25, FIG. 26, and FIG. 27 are diagrams illustrating data for describing reasons of advantages of the crossed-Nicol. FIG. 25 includes diagrams illustrating results of observations of a surface of a ham that spuriously represents the biological surface with the respective configurations illustrated in FIG. 21. The measurement wavelength is 1600 nm that is a wavelength relatively large in absorptance of light by the water.

FIG. 26 includes diagrams illustrating wavelength dependences of reflectivities in respective optical configurations illustrated to correspond to the images illustrated in FIG. 25 and illustrating characteristics distinguished by a presence/absence of water.

Furthermore, FIG. 27 includes diagrams illustrating wavelength dependences of values of (reflectivity without water/reflectivity with water) in respective optical configurations illustrated to correspond to the images illustrated in FIG. 25.

It is seen from FIG. 25 that the optical configuration with the crossed-Nicol is less likely to be affected by the water on the biological surface. For example, it is seen that the optical configuration with the crossed-Nicol can easily obtain information of the biological surface layer.

Seeing a difference between the reflectivities of the infrared lights with the wavelengths of 1070 nm regarding a region where a lot of water is present and a region where a little water is present on the biological surface in FIG. 26, it is seen that the crossed-Nicol optical configuration has a small difference between the two. For example, it is seen that the crossed-Nicol optical configuration is less likely to be affected by the water including the bodily fluid on the biological surface.

As illustrated in FIG. 27, it is seen that the crossed-Nicol optical configuration hardly shows an absorption spectrum (peak) of a water. Since this result matches with the results in FIG. 25 and FIG. 27, it is seen that an effect of water including the bodily fluid on the biological surface can be reduced in the optical configuration with the crossed-Nicol.

Typically, the s polarization has a reflectivity larger than that of the p polarization; therefore, it can be said that a method using the s polarization is more appropriate for the measurement using the reflected light.

As described above, the embodiment ensures clearly observing the biological surface without being affected by, for example, the regular reflection light from the bodily fluid flown out to the biological surface and the spectral characteristics belonging to the bodily fluid itself (or by reducing the effect of the spectral characteristics).

Seventh Embodiment

A seventh embodiment includes the following configuration in the configuration illustrated in FIG. 1A and FIG. 21 in order to make the technique described in the sixth embodiment be easily used.

An observation apparatus according to the embodiment is configured to be switchable between a first state (a first optical configuration) and a second state different from the first state. In the first state, a first polarizer 21a or 21b is arranged in the optical path of a light with which the tissues 11 of the organism are irradiated from the light source apparatus (irradiator) 17 in FIG. 1A and a second polarizer 21c having a phase difference with respect to a polarizing angle of the first polarizer 21a or 21b in the optical path of the light entering the camera (the detector and the light receiver) 15 from the tissues 11 is arranged. For example, the observation apparatus includes a mechanism (the switch 19) that can change the polarizing angle of the second polarizer 21c.

For example, the observation apparatus can obtain the bodily fluid data obtained, for example, by the first embodiment after the switch 19 switches the first state in which there is a phase difference with the polarizing angle of the first polarizer 21a or 21b in the optical path of the light entering the camera (the light receiver) 15 from the tissues 11 to the second state in which there is no phase difference (zero phase difference) or a little phase difference.

Meanwhile, the observation apparatus can perform an observation of the biological surface with a restrained (or reduced) effect of the bodily fluid as described in the fifth embodiment by switching to the first state with the switch 19.

With the embodiment, the light with which the tissues 11 are irradiated from the light source apparatus 17 can be the s polarization by changing the polarizing angle of the first polarizer 21a or 21b with the switch 19.

It should be noted that the processing and controls described above can be achieved by software processing by a Central Processing Unit (CPU) and a Graphics Processing Unit (GPU) and hardware processing by an Application Specific Integrated Circuit (ASIC) and an Field Programmable Gate Array (FPGA).

In the embodiments described above, the configurations illustrated in the attached figures or the like should not be construed as a limiting sense, and can be appropriately changed within a range where effects are provided. Additionally, changes can be appropriately made as long as not departing from a range of purpose.

Each of the components can be conveniently selected, and the invention including the configuration selected is also included in the present invention.

A program for achieving each function described in the embodiments may be recorded in a computer readable recording medium. Then, processing on each of the devices may be performed by causing a computer system to read and execute the program recorded in this recording medium. It should be noted that, the "computer system" here includes hardware, such as OS and peripherals.

REFERENCE SIGNS LIST

A Observation apparatus
7 Display
3 Data generator
3-1 First data generator
3-2 Second data generator
3-3 Comparison calculator
3-5 Real-time (comparison) data generator
3-5a Data change detector
3-6 Live display data generator
7 Display
10 Stage
11 Tissue
17 Light source apparatus
15 Imaging apparatus
19 Switch
21 Polarizing plate Every published material, patent, and patent application referred in this description are incorporated herein directly by reference.

The invention claimed is:

1. An observation apparatus that observes tissues, the observation apparatus comprising:
   a generator that generates first data which corresponds to a first absorptance or a first transmittance with respect to a water and second data which corresponds to a second absorptance or a second transmittance with respect to the water, the first data being obtained by irradiating a tissue with a first infrared light with a first wavelength; and
   a comparison calculator that generates an image including a presence of a bile flowing out a surface of the tissue obtained by performing dividing processing or subtracting processing on the first data by the second data.

2. The observation apparatus according to claim 1, wherein the first wavelength is shorter than 1300 nm.

3. The observation apparatus according to claim 1, wherein the second wavelength is a wavelength longer than a wavelength of the first wavelength and from 1250 nm to 1600 nm.

4. The observation apparatus according to claim 1, wherein the second wavelength is a wavelength from 1400 nm to 2000 nm.

5. The observation apparatus according to claim 1, wherein the second wavelength is a wavelength from 1250 nm to 1400 nm.

6. The observation apparatus according to claim 1, comprising
   a data change detector that detects a change in the bodily fluid data.

7. The observation apparatus according to claim 1, comprising
   a real-time comparison data generator that generates the bodily fluid data on a real-time basis.

8. The observation apparatus according to claim 7, wherein the real-time comparison data generator performs dividing processing or subtracting processing on the bodily fluid data generated before a predetermined time by the bodily fluid data generated after the predetermined time.

9. The observation apparatus according to claim 1, comprising
a live display data generator that generates data for live display based on image data obtained by performing arithmetic processing on a plurality of pieces of the bodily fluid data.

10. The observation apparatus according to claim 9,
wherein the live display data generator generates the data for live display based on image data obtained by performing arithmetic processing on a first of the bodily fluid data at a first timing and a second of the bodily fluid data at a second timing different from the first timing.

11. The observation apparatus according to claim 10, comprising
a data storage that stores the first bodily fluid data as reference data,
wherein the live display data generator generates the data for live display based on image data obtained by performing arithmetic processing on the bodily fluid data sequentially generated by changing the second timing, and the reference data.

12. The observation apparatus according to claim 10,
wherein the live display data generator calculates first difference data between the first bodily fluid data and the second bodily fluid data and second difference data between the second bodily fluid data and third bodily fluid data that is obtained at a third timing after the second timing.

13. The observation apparatus according to claim 9, comprising
a display that displays a live moving image based on data obtained from the live display data generator.

14. The observation apparatus according to claim 9, comprising
an analyzer that estimates a source of leakage of a bodily fluid using data obtained from the live display data generator.

15. The observation apparatus according to claim 1, comprising
a noise region remover that hides a noise region other than a display region based on the bodily fluid data.

16. The observation apparatus according to claim 1, comprising:
an irradiator that irradiates the tissue with the first infrared light and the second infrared light; and
a detector that detects a light from the tissue irradiated with a light by the irradiator,
wherein the detector sends a detected detection result to the data generator.

17. The observation apparatus according to claim 16, comprising:
a first polarizer arranged in an optical path of a light with which the tissue is irradiated from the irradiator; and
a second polarizer that has a phase difference with respect to a polarizing angle of the first polarizer, the second polarizer being arranged in an optical path of a light that enters the detector from the tissue,
wherein the observation apparatus is configured to be switchable between a first state having the second polarizer arranged and a second state not having the second polarizer arranged, the first state having the second polarizer arranged, the second state being different from the first state.

18. The observation apparatus according to claim 17,
wherein the first data and the second data are generated in the second state.

19. The observation apparatus according to claim 17,
wherein the second state has a phase difference of 0 degrees between polarizing angles of the first polarizer and the second polarizer.

20. The observation apparatus according to claim 17,
wherein the first polarizer has a polarizing angle set such that a light with which the tissue is irradiated becomes an s polarization.

21. The observation apparatus according to claim 1, wherein the bodily fluid includes a bile.

22. An observation system comprising:
the observation apparatus according to claim 1; and
a display that displays the generated bodily fluid data.

23. A non-transitory computer-readable computer medium storing a program used for an observation apparatus that observes tissues, the program causes a computer to execute:
a step of comparing first data which corresponds to a first absorptance or a first transmittance with respect to a water with second data which corresponds to a second absorptance or a second transmittance with respect to the water, the first data being obtained by irradiating a tissue with a first infrared light with a first wavelength, the second data being obtained by irradiating the tissue with a second infrared light with a second wavelength; and
a step of generating an image including a presence of a bile flowing out a surface of the tissue based on dividing or subtracting the first data by the second data.

24. A data processing apparatus that processes data regarding tissues of an organism, the data processing apparatus comprising:
a data generator that generates first data which corresponds to a first absorptance or a first transmittance with respect to a water and second data which corresponds to a second absorptance or a second transmittance with respect to the water, the first data being obtained by irradiating an tissue with a first infrared light with a first wavelength, the second data being obtained by irradiating the tissue with a second infrared light with a second wavelength; and
a comparison calculator that generates an image including a presence of a bile flowing out a surface of the tissue based on dividing or subtracting the first data with by the second data.

* * * * *